United States Patent [19]
Nonami et al.

[11] Patent Number: 5,948,129
[45] Date of Patent: Sep. 7, 1999

[54] METHOD FOR PREPARING A MOLDED GLASS MATERIAL FOR USE IN THE MANUFACTURE OF LIVING TISSUE REPLACEMENT

[75] Inventors: Toru Nonami; Tatsuji Sano, both of Chiba; Sadami Tsutsumi, Kyoto; Tetsuo Urabe, Ibaraki; Masahiro Fukuma, Hirakata, all of Japan

[73] Assignee: TDK Corporation, Tokyo, Japan

[21] Appl. No.: 08/736,247

[22] Filed: Oct. 24, 1996

Related U.S. Application Data

[63] Continuation of application No. 08/245,038, May 17, 1994, abandoned.

[30] Foreign Application Priority Data

| May 17, 1993 | [JP] | Japan | 5-139099 |
| Aug. 6, 1993 | [JP] | Japan | 5-214944 |
| Dec. 29, 1993 | [JP] | Japan | 5-353680 |
| Mar. 28, 1994 | [JP] | Japan | 6-080966 |

[51] Int. Cl.$^6$ ................................................. C03B 11/00
[52] U.S. Cl. ............................... 65/33.1; 65/102; 65/111; 65/305; 433/229; 623/901; 264/16; 249/54
[58] Field of Search ...................... 65/33.1, 102, 111, 65/61, 286, 305, 362, 375, 21.2, 17.3, 17.6, 83, 126, 137; 106/35; 501/55, 72, 25, 4; 433/229, 201.1, 228.1; 623/16, 66, 901; 264/16, 19, 907; 249/54

[56] References Cited

U.S. PATENT DOCUMENTS

| 4,560,666 | 12/1985 | Yoshida et al. | 65/33.7 |
| 4,780,081 | 10/1988 | Enomoto et al. | 433/174 |
| 4,783,429 | 11/1988 | Shibuya et al. | 501/5 |
| 4,871,384 | 10/1989 | Kasuga | 65/30.1 |
| 4,960,733 | 10/1990 | Kasuga et al. | 501/5 |
| 5,066,619 | 11/1991 | Kasuga et al. | 106/35 |
| 5,108,477 | 4/1992 | Cornelius et al. | 65/17.3 |
| 5,125,971 | 6/1992 | Nonami et al. | 106/35 |
| 5,232,878 | 8/1993 | Kasuga et al. | 106/35 |
| 5,344,456 | 9/1994 | Nonami et al. | 623/16 |
| 5,356,436 | 10/1994 | Nonami et al. | 623/901 |

FOREIGN PATENT DOCUMENTS

| 0 231 773 | 8/1987 | European Pat. Off. . |
| 0 401 793 | 12/1990 | European Pat. Off. . |
| 42 07 180 | 9/1992 | Germany . |
| 62-231655 | 10/1987 | Japan . |
| 4- 36107 | 6/1992 | Japan . |

OTHER PUBLICATIONS

Second International Congress on Dental Materials, Nov. 1993, pp. 13–14 and 309.
The Journal of the Japan Society of Dental Technics Excerpt of the Lecture, Aug. 7, 1993, M. Fukuma, et al., "Studies of the Application of CaO–SiO2–MgO Glass to Dental Crowns".
The Journal of the Japan Research Society of Dental Materials and Appliances, vol. 12, Special Issue 22, Sep. 1993, T. Nonami, et al., "Basic Studies of Press–Formable CaO–SiO2–MgO Glass Ceramics For Dental Crowns".
M. Fukuma et al., "Study on the Application of CaO–SiO–MgO Glass to Dental Crowns, First Report: Material Properties". Aug. 1993.
U.S. Application No. 08/245038.
U.S. Application No. 08/736247.

*Primary Examiner*—Steven P. Griffin
*Attorney, Agent, or Firm*—Oblon, Spivak, McClelland, Maier & Neustadt, P.C.

[57] ABSTRACT

A living tissue replacement of crystallized glass having bioaffinity and mechanical strength is briefly obtained simply by pressure molding or machining without using a special equipment. A glass material having a softening point below its crystallization temperature and exhibiting viscous flow at temperatures below its melting point is heated at a temperature above its Tg and pressed at the temperature to mold to a desired shape, thereby manufacturing a living tissue replacement such as a dental crown. Molding can be done under a pressure of up to 20 MPa.

29 Claims, 12 Drawing Sheets

(a)

(b)

(c)

(d)

(e)

(a)

(b)

(c)

METHOD FOR PREPARING A MOLDED GLASS MATERIAL FOR USE IN THE MANUFACTURE OF LIVING TISSUE REPLACEMENT

This application is a Continuation of application Ser. No. 08/245,038, filed on May 17, 1994, now abandoned.

BACKGROUND OF THE INVENTION

1. Field of the Invention

This invention relates to living tissue replacements such as artificial dental crowns, artificial dental roots, artificial bones, bone screws, and artificial air tubes. It also relates to a method for preparing living tissue replacements, a glass material and a molding apparatus for use in the manufacture of living tissue replacements.

2. Prior Art

Various biotic ceramics are used to form living tissue replacements such as artificial dental crowns, artificial dental roots, artificial bones, artificial junctions and bone fillers. Among biotic ceramics, great attention is paid to crystallized glass or glass-ceramics because of good biological affinity and high mechanical strength. As to the crystallized glass for biological use, the following proposals have been made.

Japanese Patent Publication (JP-B) No. 69094/1992 proposes a calcium phosphate system crystallized glass for use as a dental material comprising CaO, $P_2O_5$, and Al, with the Ca/P ratio being from 0.35 to 0.49. A shape of glass is formed by centrifugal casting and then heat treated for crystallization. Since this method utilizes centrifugal casting for shaping of glass, the glass must be melted, making it difficult to use a high strength glass composition having a high melting point. Then, the crystallized glass of this proposal is less reliable when applied to living tissue replacements which receive substantial impacts in a repetitive manner. In fact, the calcium phosphate system crystallized glass examples disclosed in the publication are not regarded satisfactory in mechanical strength and a substantial amount of glass component leaches out. The casting process is difficult to ensure dimensional precision since glass experiences considerable shrinkage upon cooling. The casting process also allows bubbles to be introduced into the glass which is then insufficient in strength, often resulting in defective parts due to bubble inclusion. The crystallized glass of this proposal raises problems particularly when applied to artificial dental crowns. While artificial dental roots need not have a shape and size specific to an individual patient so that standard parts can be manufactured on a large scale, artificial dental crowns must be configured to a shape conformal to the deficient site of an individual patient and are thus required to be easily shaped by the dentist or dental technician with simple means. It is, however, difficult for the dentist or dental technician to perform shaping by a casting process. The casting process further has the problem that heat treatment over a long time is necessary since crystallization of glass takes place from an amorphous state after shaping by the casting process. In fact, crystallization took about 10 to 20 hours in the examples disclosed in the publication.

JP-B 36107/1992 discloses crystallized glass for use as artificial bones and dental materials. This crystallized glass has a non-calcium phosphate system composition free of $P_2O_5$. It is prepared by molding glass powder, followed by firing and crystallization treatment. With the process of molding and firing glass powder, it is difficult to prepare dental crowns and other parts of complex shape. Since the molding step uses an isostatic press and the firing step uses a high temperature of 1,050° C. as described in the publication, this process is quite difficult to practice in the dental office. The process takes a long time since the firing step uses a slow heating rate of 30 to 60°C./hour and a slow cooling rate of 30 to 120° C./hour. Dimensional precision is low since firing entails a large shrinkage factor. Even when a high strength composition is used, firing of glass powder after molding tends to lower strength. Preparation of glass powder requires cumbersome operation and considerable costs because molten glass must be converted into ribbon shape as by passing through water-cooled rollers. In addition, many voids are left after firing.

Furthermore, wollastonite and diopside are precipitated in the crystallized glass of JP-B 36107/1992 although the amount of diopside precipitated is not specified therein except for only one datum of 40% in Example.

Japanese Patent Application Kokai (JP-A) No. 70244/1987 discloses a dental crown-forming material comprising crystallized glass. It is prepared by casting a molten raw material into a mold and heat treating the molded material. At the end of heat treatment, $Na.Mg_3(Si_3AlO_{10})F_2$ grains (mica) having improved mechanical workability and $Li_2O.Al_2O_3.2SiO_2$ grains (β-eucryptite) and $Li_2O.Al_2O_3.4SiO_2$ grains (β-spodumene) having improved mechanical strength precipitate in this dental crown-forming material. $TiO_2$ and $ZrO_2$ are added for controlling crystal growth and improving mechanical strength and $Fe_2O_3$ and MnO are added to control color. The examples disclosed in this publication achieve a flexural strength of 2,000 to 2,700 $kg/cm^2$, which is still insufficient. The use of a casting process for molding suffers from problems as mentioned above.

JP-A 12637/1987 discloses a glass ceramic dental crown which is prepared by molding molten glass followed by heat treatment for causing mica and spodumene crystal phases to precipitate out. Although the glass ceramic is alleged to be improved in machinability and mechanical strength, no exemplary evaluation of machinability and mechanical strength is disclosed. The use of a casting process for molding suffers from problems as mentioned above.

JP-A 174340/1991 discloses an artificial dental crown formed of a glass ceramic composition comprising a calcium-potassium mica crystal and at least one of enstatite, akermanite, and diopside crystals, or comprising a calcium-potassium-sodium mica crystal and at least one of enstatite, akermanite, diopside, anorthite, and richterite crystals. This glass ceramic is alleged to have a hardness approximate to natural teeth and improved mechanical strength, mechanical workability, corrosion resistance and light transmittance. The glass ceramic of such a crystal structure has insufficient gloss and raises an aesthetic problem when used as dental crowns. Also bioactivity is insufficient. The publication describes that the step of shaping glass ceramic to a dental crown configuration includes a casting process as well as machining although the casting process raises problems as mentioned above.

JP-A 88744/1991 discloses a glass ceramic composition comprising a barium-calcium mica crystal and at least one of enstatite, forsterite, and diopside crystals or comprising a barium-calcium mica crystal and at least one of enstatite, forsterite, diopside, and tetragonal zirconia crystals. In the examples therein, a maximum flexural strength of 5,000 $kg/cm^2$ is reported. However, this glass ceramic is intended for machinable ceramic, but not for application to biotic materials such as artificial dental crowns. In fact, the glass ceramic of such a crystal structure has insufficient gloss and raises an aesthetic problem when used as dental crowns.

SUMMARY OF THE INVENTION

An object of the present invention is to make it possible to prepare a living tissue replacement of crystallized glass having both biological affinity and mechanical strength without a special mechanical means and within an acceptably short time. Another object of the invention is to make it possible to prepare a living tissue replacement of crystallized glass having both biological affinity and mechanical strength by mechanical working in a simple manner.

According to a first aspect, the present invention provides a glass material for use in the manufacture of a living tissue replacement, which has a crystallization temperature and a softening point which is lower than the crystallization temperature and exhibits viscous flow at temperatures below its melting point.

Preferred embodiments are described below.

Preferably, the glass material has a non-calcium phosphate system composition comprising silicon oxide, calcium oxide, and magnesium oxide. The total content of silicon oxide, calcium oxide, and magnesium oxide, calculated as $SiO_2$, CaO, and MgO, respectively, is at least 70% by weight, more preferably at least 80% by weight of the composition. The contents of the respective components are 40 to 70% by weight of $SiO_2$, 20 to 50% by weight of CaO, and 8 to 30% by weight of MgO based on the total content.

Preferably, the glass material further contains at least one element selected from the group consisting of Na, K, B, Al, Ba, Fe, Zr, Ce, Au, Ag, Cu, Ti, Cr, Ni, Li, Bi, Co, V, Pd, Pt, Sn, Sb, F, Mn, Sr, Nb, Ta, Y, and Ca. More preferably, the glass material contains up to 20% by weight of $TiO_2$ or up to 10% by weight of $ZrO_2$.

Preferably, the glass material has a crystallization temperature of up to 1,000° C. The glass material exhibits a distortion of at least 20% at a temperature of up to 1,000° C. and a pressure of up to 20 MPa.

Typically, the living tissue replacement is an artificial dental crown.

According to another aspect, the invention provides a method for preparing a living tissue replacement comprising the step of molding a glass material at a temperature below its melting point under pressure by utilizing a viscous flow phenomenon.

Preferred embodiments are described below.

Preferably, the glass material prior to pressure molding has a first crystallinity and the living tissue replacement has a second crystallinity greater than the first crystallinity. The glass material is typically as set forth in the first aspect.

Preferably, the method further includes the step of effecting crystallization treatment on the glass material during or after the pressure molding. The method may further include the step of nucleating the glass material prior to the crystallization treatment. More preferably, the glass material is nucleated, thereafter pressure molded at a temperature not lower than its glass transition temperature, and crystallized during or after the pressure molding. Typically, pressure molding uses a pressure of up to 20 MPa and a temperature which is not higher than the crystallization temperature plus 50° C. Preferably, the glass material during pressure molding has a crystallinity of up to 50% by volume. Preferably, the glass material is pressure molded at a temperature which is up to 0.8 times its melting point. Preferably, the glass material during pressure molding has a viscosity of up to $10^9$ poise. At the end of pressure molding of the glass material, the pressure is released while the glass material is at a temperature not lower than its glass transition temperature.

In one preferred embodiment, the method uses a molding apparatus including a mold and a punch. The mold includes a molding cavity and a bore through which the punch is inserted, the bore being in fluid communication with the molding cavity through a sprue. Then the glass material is placed in the bore and the punch is urged into the bore against the glass material for effecting pressure molding. The mold further includes a vent in fluid communication with the molding cavity. The bore is defined by an inner surface which extends substantially parallel to the pressure applying direction. The bore inner surface has a taper of up to ⅕. The sprue is inclined relative to the pressure applying direction. The sprue has a cross-sectional shape corresponding to the shape of the molding cavity. The mold may further include a liner covering at least a portion of the bore inner surface, the liner being made of a high strength material having a higher compression strength than the mold body. The punch may further include a cover forming at least a portion of the surface of the punch opposed to the bore inner surface, the cover being made of a high strength material having a higher compression strength than the mold body. The mold body has a compression strength of up to 20 MPa at the end of pressure molding. The high strength material has a compression strength of at least 15 MPa.

In a further preferred embodiment, the method for preparing a living tissue replacement further includes the step of machining the glass material after the crystallization treatment.

According to a third aspect, the present invention provides a method for preparing a living tissue replacement comprising the steps of: crystallizing a glass material as defined in the first aspect and machining the crystallized glass material.

Also contemplated herein are living tissue replacements prepared by the above mentioned methods. Typically, diopside grains are dispersed in the living tissue replacement.

Also contemplated herein is a living tissue replacement molding apparatus which is used in the molding step of the above-mentioned method for preparing a living tissue replacement.

ADVANTAGES

According to the invention, a living tissue replacement is prepared by molding a glass material at a temperature between its glass transition temperature (inclusive) and its melting point (exclusive) under a certain pressure into a desired shape such as a dental crown while utilizing the viscous flow phenomenon that the glass exhibits at the temperature. By utilizing the viscous flow, the glass material can be molded to a desired shape under a pressure of up to about 20 MPa.

The glass material used herein is preferably of a composition capable of creating diopside ($CaO.MgO.2SiO_2$) crystals. We have found that glass of this composition is a bioactive material which has a low viscosity at temperatures from its glass transition temperature to near its crystallization temperature, especially from its softening point to near its crystallization temperature so that it is prone to pressure molding. Glass materials having a composition within the scope of JP-B 36107/1992 are not sufficiently low in viscosity at such temperatures.

The present invention has the following advantages.

(1) Glass material can be molded under pressure at a temperature of lower than its melting point, preferably at a temperature lower than nearly its crystallization temperature, for example, 1,000° C. or lower, especially 900° C. or lower. Then the glass material can be heated in conventional furnaces which are commonly found in dental offices. The glass material can be molded in air without any deterioration by oxidation, eliminating a need for atmosphere control. The glass material provides smooth mold release. Even when metal compounds are used as a coloring agent, they are not burnt.

(2) Glass material can be molded under a low pressure of up to 20 MPa, especially up to 1 MPa. This eliminates a need for special pressurizing means and enables molding by merely using a hand press or weight, for example. A high strength mold is no longer needed. The glass material can be easily molded in ordinary dental offices.

(3) The present invention prefers the use of crystallized glass having a composition in the diopside field, which has extremely high strength, but an extremely high melting point (often above 1,4000° C.) so that its casting is almost impossible. The pressure molding process of the invention can form crystallized glass having a composition in the diopside field without heating to extremely high temperatures. The crystallized glass having a composition in the diopside field is so bioactive that it may be adequate as living tissue replacements.

(4) As opposed to a process of molding and firing glass powder, the present invention requires neither special mold nor special equipment like a continuous isostatic press (CIP). Conventional dental casting molds can be used.

(5) The prior art process of molding and firing glass powder is difficult to produce parts to precise dimensions because of the presence of voids in the molded parts and a substantial shrinkage factor upon firing. The present invention eliminates voids since glass material is molded in bulk under pressure. The glass used herein has a very low coefficient of thermal expansion. There are thus available molded parts or living tissue replacements reflecting the mold cavity faithfully, that is, at high precision.

(6) The prior art process of molding glass powder is difficult to produce complex shaped parts like dental crowns whereas the present invention is effective for producing complex shaped parts as easily as the casting process because glass material is softened and fluidized in bulk. The molded parts are satisfactorily homogeneous. As opposed to the casting process, few bubbles are found in the molded parts which have high strength and the percentage of defective parts is minimized.

(7) As opposed to the casting process, the glass material is not melted. It is then possible to effect nucleation and/or crystallization on the glass material prior to molding as shown in FIGS. 1(a), 1(d) and 1(e). More particularly, when the invention is applied to the manufacture of a dental crown, the glass material which has been nucleated and/or crystallized can be delivered to the dentist or dental technician, enabling substantial reduction of the time taken from molding to completion of a dental crown. The glass material of the invention has a short crystallization time so that crystallized glass parts can be produced within a short time even when crystallization is effected during or after pressure molding as shown in FIGS. 1(b) and 1(c). For example, a prior art process of molding and crystallizing amorphous glass required about 6 to 12 hours whereas the present invention can complete a dental crown of crystallized glass within only about 3 hours.

(8) The invention insures sufficiently high strength because homogeneous glass is directly molded and crystallized without melting. If part of glass material is once melted upon molding, there is a likelihood that the glass as crystallized would not have a homogeneous grain structure and hence, sufficient strength. By molding glass material at a temperature which is lower than 0.8 times its melting point, local melting of the glass material can be restrained nearly completely. The present invention also eliminates a likelihood that glass be devitrified by melting or be distorted to lose strength upon cooling.

JP-A 231655/1987 discloses preparation of a dental instrument by molding a ceramic material or alloy which can be plasticized by heating. No reference is made to crystallized glass therein. In one example of this publication, a dental crown is prepared by molding a mixture of a glass-forming base material, an aluminum oxide for imparting necessary strength, a flux selected from $K_2O$, $Na_2CO_3$, CaO, and $B_2O_3$, and a plasticizer such as glycerin. The example uses aluminum oxide for insuring strength probably because the glass is not crystallized. Nevertheless, the thus obtained material has insufficient strength as compared with the crystallized glass obtained in the present invention. Even if one attempts to crystallize the material of this publication, it is difficult to achieve high strength because inclusion of the flux restrains homogeneous crystallization. If a metal compound is added to glass as a coloring agent as is often the case, a heating temperature in far excess of 1,000° C. upon compression as described in the publication causes sublimation of the coloring agent, failing to provide a desired color.

According to the present invention, a specific amount of $TiO_2$ is added to a glass material comprised of $SiO_2$, CaO, and MgO as main components for achieving a substantial improvement in machinability. Strength is significantly improved by adding $ZrO_2$ along with $TiO_2$. Glass material of such composition is easy in machining or mechanical working and ensures precise dimensions after machining. Therefore, the glass material lends itself to precision machining utilizing a CAD/CAM system and is adequate for the manufacture of artificial dental crowns and roots. When the glass material is processed by the pressure molding method utilizing viscous flow as defined herein, parts of any desired dimensions are obtained without sacrificing strength. Waste of the glass material upon machining can be minimized, contributing to a cost reduction.

In the apparatus for molding glass material, a bore 23 through which a punch 4 is inserted has an inner surface which is slightly tapered or not tapered as shown in FIGS. 3 to 5 for preventing back flow of softened glass material 3 through a gap between the bore 23 and the punch 4. This minimizes the necessary loading of glass material.

Also a mold 2 having a cavity 21 and a vent 24 in fluid communication therewith as shown in FIGS. 3 to 5 allows part of the glass material to escape under pressure so that the mold cavity may be readily filled with the glass material, facilitating production of a molded shape faithful to the mold cavity under a low pressure. Since the vent 24 prevents application of excessive pressure to the mold 2 during pressure molding, it is also effective for preventing the mold 2 from cracking, resulting in a drastic drop of percent generation of defective parts.

In an embodiment wherein a sprue 22 connecting the molding cavity 21 and the punch-receiving bore 23 in fluid communication is inclined relative to the pressing direction as shown in FIG. 5, the mold cavity 21 is readily filled with the glass material, facilitating production of a molded shape faithful to the mold cavity under a low pressure. It is also effective for preventing the mold 2 from cracking during pressure molding.

The preferred embodiment where the sprue 22 has a cross-sectional shape corresponding to the shape of the molding cavity facilitates production of a molded shape more faithful to the mold cavity under a low pressure.

In the preferred embodiment wherein the mold 2 further includes a liner 25 covering at least a portion of the bore 23 inner surface, the liner being made of a high strength material having a higher compression strength than the mold body as shown in FIGS. 10 to 12, the high strength liner 25 is effective for preventing the mold 2 from cracking and the mold body made of a material having a relatively low compression strength is effective for preventing rupture of the molded part upon withdrawal from the mold. In the further preferred embodiment wherein a reinforcement 45 forms at least a portion of the surface of the punch 4 opposed to the bore 23 inner surface, the reinforcement being made of a high strength material having a higher compression strength than the mold body as shown in FIGS. 13(*a*), 13(*b*) and 13(*c*), any rupture of the punch 4 is prevented during molding.

DETAILED DESCRIPTION OF THE INVENTION

Glass Material

Figure 1:
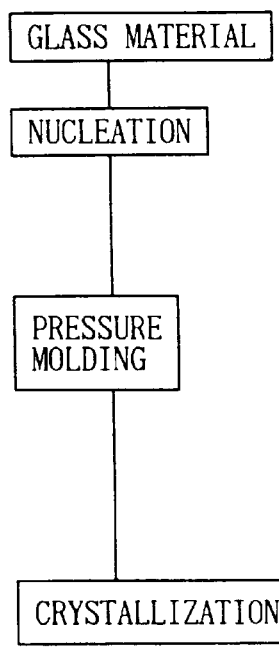
FIGS. 1(*a*) to 1(*e*) are flow diagrams showing steps of preparing a living tissue replacement according to different embodiments of the invention.
Figure 1:
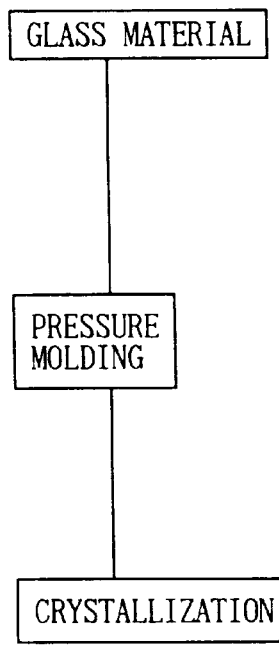
Figure 1:
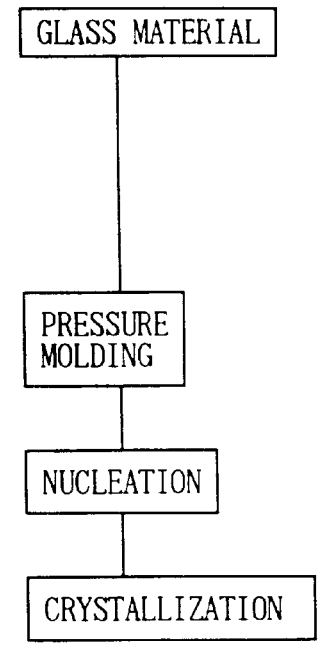
Figure 1:
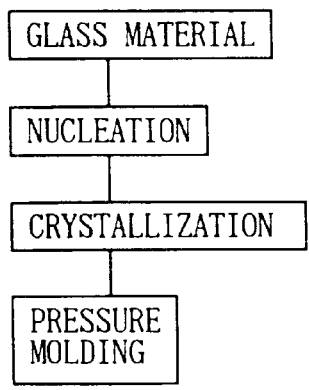
Figure 1:
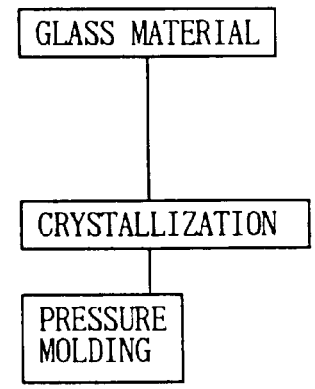

The glass material which is used for the manufacture of living tissue replacements according to the present invention is not particularly limited in composition. A choice may be made of various compositions which are capable of pressure molding utilizing viscous flow. Exemplary preferred compositions are those from which at least one of $CaO$—$MgO$—$SiO_2$ (monticellite), $2CaO$—$MgO$—$2SiO_2$ (akermanite), $2(Mg,Ca)O$—$SiO_2$ (forsterite), $\beta$-$(Ca,Mg)O$—$SiO_2$ (wollastonite), $Na_2O$—$Al_2O_3$—$2SiO_2$ (nephelite), $Na_2O$—$Al_2O_3$—$6SiO_2$ (albite), $Na_2O$—$Al_2O_3$—$4SiO_2$ (jadeite), $MgO$—$TiO_2$, $Al_2O_3$—$SiO_2$ (andalusite), $3Al_2O_3$—$2SiO_2$ (mullite), $Cao$—$Al_2O_3$—$2SiO_2$ (anorthite), $2CaO$—$Al_2O_3$—$SiO_2$ (gehelenite), and $3CaO$—$Al_2O_3$—$3SiO_2$ (grossularite) can precipitate out. A glass material having a non-calcium phosphate system composition comprising silicon oxide, calcium oxide, and magnesium oxide and having a softening point lower than its crystallization temperature is preferred because of ease of pressure molding.

More preferably, in the glass material comprising silicon oxide, calcium oxide, and magnesium oxide, the total content of silicon oxide, calcium oxide, and magnesium oxide, calculated as $SiO_2$, $CaO$, and $MgO$, respectively, is at least 70%, especially at least 80% by weight of the entire glass material. The remainder is generally a coloring agent, crystallization promoter and the like. If the total content of $SiO_2$, $CaO$, and $MgO$ is less than 70% by weight, some of the advantages of the invention including bioactivity and viscous flow would be lost and strength would become lower.

The contents of the respective components are 40 to 70%, especially 53 to 70% by weight of $SiO_2$, 20 to 50%, especially 20 to 35% by weight of $CaO$, and 8 to 30%, especially 10 to 25% by weight of $MgO$ based on the total content of $SiO_2$, $CaO$, and $MgO$. Outside the range, (1) a viscosity drop during pressure molding would be insufficient, leaving a likelihood of the glass material being broken under applied pressure; (2) vitrification would be retarded; (3) a necessary viscosity drop would occur at higher temperature, to which the material must be heated before pressure molding can be effected; (4) melting temperature would become higher; (5) the temperature at which diopside grains precipitate would become higher; and (6) the type and amount of precipitating grains would largely vary.

More particularly, a too low content of $SiO_2$ would retard vitrification and lower strength whereas a too high content of $SiO_2$ would elevate the melting temperature. A too low content of $CaO$ would retard grain precipitation whereas a too high content of $CaO$ tends to incur devitrification and reduce the amount of diopside grains precipitated. A too low content of $MgO$ would reduce the amount of diopside grains precipitated whereas a too high content of $MgO$ tends to incur devitrification.

In addition to these oxides, various elements or compounds may be added to the glass material as a coloring agent, crystallization promoter or processing aid. Preferred is at least one element selected from the group consisting of Na, K, B, Al, Ba, Fe, Zr, Ce, Au, Ag, Cu, Ti, Cr, Ni, Li, Bi, Co, V, Pd, Pt, Sn, Sb, F, Mn, Sr, Nb, Ta, Y, and Ca. Among these elements, Al, Fe, Ce, Ag, Cu, Ti, Cr, F, Mn, Sr, Nb, Ta, Y and Ca function as a coloring agent, Zr, Au, Ag, Pt, Ti and F function as a crystallization promoter, and Na, Li, Ti, K, B, and Al are effective for improving processability. The processing aids are to facilitate vitrification and lower viscosity.

These additive elements may be added in elemental form or as compounds, with preferred exemplary compounds being oxides, chlorides, nitrates and sulfates.

More particularly, $TiO_2$ is advantageously added when the glass material as crystallized is to be machined because addition of titanium dioxide is effective for improving strength and machinability and facilitating crystallization. It is also effective for improving aesthetic appearance by imparting lustrous outer appearance as well as color tone and light transmittance similar to natural teeth. The glass material is thus suitable for dental crowns and artificial bones. Preferably the glass material contains up to 20% by weight of $TiO_2$. A $TiO_2$ content of 7 to 15% by weight is most preferred for increasing strength, with a flexural strength of higher than about 300 MPa being achieved for example. A too low content of $TiO_2$ would be ineffective for its addition purpose, that is, crystallization would be insufficient and strength would lower.

Preferably, $ZrO_2$ is added to the glass material along with $TiO_2$. The addition of $ZrO_2$ improves strength and machinability and is advantageous when the molded part is to be machined. The content of $ZrO_2$ is preferably up to 10% by weight of the glass material, with maximum strength being available at a $ZrO_2$ content of 0.1 to 2% by weight. A too low content of $ZrO_2$ would be ineffective for its addition purpose, that is, strength enhancement would be insufficient. A too high content of $ZrO_2$ would detract from machinability. The combined addition of $TiO_2$ and $ZrO_2$ is effective for improving strength and machinability, with a flexural strength of higher than about 300 MPa being readily achieved for example.

The glass material containing an adequate amount of $TiO_2$ or $TiO_2$ plus $ZrO_2$ has high strength as mentioned above and is suitable for use in artificial bones and dental bridges as well as inlays and onlays.

By adding Sr, Nb, Ta, Y, Ca and Fe, the glass material can be colored to an appropriate tone as dental crowns. The content of these elements is preferably up to 5% by weight in total provided that the elements are calculated as SrO, $Nb_2O_3$, $Ta_2O_5$, $Y_2O_3$, CaO, and $Fe_2O_3$. In excess of 5% by weight, strength would be lower.

Crystallization is promoted by adding silver and gold compounds such as AgCl, $Ag_2O$ and $AuCl_3$ in a total amount of 0.01 to 1.0% by weight. Excess addition of these compounds would cause undesirable coloring and overcrystallization.

The glass material has a softening point and a crystallization temperature wherein the softening point is lower than the crystallization temperature, preferably by 20° C. or more, more preferably by 50° C. or more. Pressure molding would sometimes be difficult when the softening point is lower than the crystallization temperature by only a slight difference.

The glass material preferably has a crystallization temperature (Tx) of up to 1,000° C., more preferably up to 900° C. and generally higher than 600° C. The benefits of the invention are lost if the crystallization temperature is extremely high.

Possible molding and crystallization at temperatures below 1,000° C. eliminates the disadvantage associated with high temperatures above 1,050° C. that reaction between the investment compounds and the glass materials can occur and even the investment compounds themselves start deterioration in strength especially for those glass materials of phosphate and cristobalite systems.

In general, the glass material has a softening point (Td) of at least 500° C. and a glass transition temperature (Tg) of 400 to 900° C.

Desirably the glass material can undergo a distortion or deformation of 20% or more, even 30% or more, and in some cases 60% or more at a temperature of preferably up to 1,000° C., more preferably up to 900° C. and a pressure of preferably up to 20 MPa, more preferably up to 5 MPa, further preferably up to 1 MPa, most preferably up to 0.1 MPa.

The above-mentioned distortion behavior and the relationship of softening point and crystallization temperature of glass material can be readily accomplished by suitably selecting a composition from the above-mentioned range.

The shape and size of glass material may be suitably determined depending on a particular application. For example, artificial dental crowns have an easy to mold shape and to this end, a frustoconical, cylindrical or spherical shape may be employed. To prevent entry of bubbles during molding, to prevent lowering of mechanical strength, and to produce a homogeneous molded body, a single piece of glass material is preferably used in the manufacture of a single molded body. Differently stated, it is recommended to avoid a plurality of glass material pieces or glass powders being integrally joined during molding. However, two or more glass material pieces may be used as part of the invention if necessary.

It is not intended in the present invention that a flux or plasticizer be added to glass material for softening purposes upon pressure molding.

Preparation

According to the present invention, a living tissue replacement is prepared by pressure molding, or pressure molding and machining, or machining of glass material.

The method utilizing pressure molding is described in detail, with its variants illustrated in FIG. 1.

The glass material is prepared by melting a raw material and quenching the melt. For melting, the raw material is heated in a crucible of platinum, quartz or alumina for about 10 seconds to 20 hours, preferably about 1 minute to about 2 hours. The melting temperature which depends on the composition is generally above 1,400° C. The raw material is a mixture of oxides or substances capable of forming oxides upon melting, for example, carbonates, bicarbonates and hydroxides. Upon heating, raw material components react with each other to form a composite oxide. Melting is generally done in air. The quenching method is not critical insofar as amorphous glass is obtained at the end of quenching. For example, the melt is poured to sheet iron, carbon, water or mold. The mold may be made of dental investment materials such as cristobalite, calcium phosphate or the like.

For glass homogenization, a melting-cooling-crushing-remelting process may be repeated or high-frequency induction heating may be employed.

According to the invention, the thus prepared amorphous glass material is converted into a living tissue replacement of crystallized glass, preferably by any of the procedures shown in FIGS. 1(a) to 1(e).

The procedure shown in FIG. 1(a) includes the steps of nucleating the glass material, pressure molding it at a temperature equal to or above its glass transition temperature, and crystallizing the glass material at the same time as or after the pressure molding step.

The procedure shown in FIG. 1(b) includes the steps of pressure molding the glass material at a temperature equal to or above its glass transition temperature and crystallizing the glass material at the same time as or after the pressure molding step.

The procedure shown in FIG. 1(c) includes the steps of pressure molding the glass material at a temperature equal to or above its glass transition temperature, thereafter nucleating the glass material, and crystallizing it.

The procedure shown in FIG. 1(d) includes the steps of nucleating the glass material, crystallizing it, and thereafter pressure molding the glass material at a temperature equal to or above its glass transition temperature.

The procedure shown in FIG. 1(e) includes the steps of crystallizing the glass material and thereafter pressure molding it at a temperature equal to or above its glass transition temperature.

In these procedures, nucleation treatment is optionally effected in order to allow for uniform crystallization of glass. Although a certain composition of glass material fails to provide a desired color tone and sufficient strength due to abnormal crystal growth, nucleation treatment prior to crystallization ensures uniform crystallization. Then nucleation treatment is advantageously used when the invention is applied to dental crowns for which outer appearance is of importance. The nucleation treatment is also effective for reducing the time taken in crystallization. The conditions of nucleation treatment are not critical although heat treatment is preferably effected at a temperature near the nucleation temperature, especially the nucleation temperature ±50° C. for about 10 minutes to about 30 hours. Usually the holding temperature is about 250 to about 900° C., preferably about 400 to about 800° C. If the nucleation temperature is close to the crystallization temperature, nucleation treatment may be omitted without substantial influence.

Essential in the procedures of FIG. 1 is pressure molding which uses a temperature equal to or above the glass transition temperature of glass material, preferably a temperature at which molding is possible under a pressure of up to 20 MPa. With a proper composition chosen from the above-mentioned range, pressure molding is possible under a pressure of up to 20 MPa even if the glass material has a crystallinity as high as 50% by volume. However, if the crystallinity is up to 30% by volume, more preferably up to 8% by volume, most preferably up to 4% by volume, the glass material undergoes good flow during pressure molding, allowing a molded part of complex shape to be readily produced to precision. With too high crystallinity, the glass material has an extremely increased viscosity and is almost impossible to mold. In order to utilize the viscous flow of glass material for pressure molding, the glass material is preferably heated to a temperature at which a viscosity of lower than $10^9$ poise is reached. Such a lower viscosity facilitates molding. Since crystallization of glass material can proceed during molding depending on the temperature of pressure molding, the temperature during molding is suitably selected such that the crystallinity may fall within the desired range. This temperature varies with the time taken for molding and may be determined empirically, and most often the temperature is lower than the crystallization temperature +50° C. ($T \leq Tx+50°$ C.). To prevent excessive crystallization, it is preferred not to maintain the material near the crystallization temperature for a long time, for example, more than about 1 hour. It is to be noted that a definite crystallization temperature is not available under certain conditions, for example, when the heating rate is high or low. That is, melting can start without crystallization. In such a case, glass material is subject to pressure molding at a temperature in the range where the glass material does not melt. Preferably in order to avoid partial melting of glass material, the temperature of glass material does not exceed 0.8 times the melting point ($T \leq 0.8 \times mp$). The heating temperature at which pressure molding is carried out is at or above the glass transition temperature (Tg) and preferably at or above the softening point because below the softening point, the glass material shows insufficient flow to mold to a complex shape.

As will be described later, the living tissue replacement of the invention requires only a crystallinity of at least 10% by volume. Then, when the glass material is crystallized to a crystallinity of 10 to 50% by volume prior to pressure molding as in FIGS. 1(d) and 1(e), crystallization treatment following the pressure molding can be omitted. It is acceptable in these procedures that further crystallization takes place during pressure molding. Also, in the procedures of FIGS. 1(a) and 1(b), it is possible to simultaneously perform crystallization to 10 to 50% by volume and pressure molding.

The glass material can be molded, for example, by placing it in a mold and pressing it by a punch. The mold and punch may be made of dental investment materials based on cristobalite and phosphate cristobalite, alumina and zirconia. The mold and punch may be prepared with the ordinary skill of dentists and dental technicians.

The glass material may be heated by placing it in a pre-heated mold or by placing it in a mold and introducing the mold into a furnace. After the glass material has been heated to the predetermined temperature, it is subject to pressure molding. A hot press technique may be used for heating and pressing purposes. In an alternative technique, once heated, the mold is taken out of the furnace and a pressure force is then applied. This technique is effective for improving productivity because a plurality of molds each loaded with glass material can be concurrently heated in the furnace. Application of pressure force to the glass material may be initiated either before or after the maximum temperature during molding is reached. The former is advantageous in shortening the molding step because molding begins at the same time as the glass material softens. If a necessary deformation is achieved before the maximum temperature is reached, pressurization may be interrupted at that point of time, which contributes to a further time saving. The latter ensures homogeneity after molding because the glass maintains a constant viscosity during pressurization. Since a pressure force is applied subsequent to a glass viscosity drop, the mold is prevented from fracture. A pressure force is maintained until the glass material has been deformed to faithfully reflect the mold cavity, often for about 5 to 20 minutes although the exact time varies with press means and temperature.

At the end of molding, the pressure force is preferably released while the glass material remains above its glass transition temperature, more preferably while the glass material temperature is above its softening point. If the pressure force is maintained after the temperature has lowered below the glass transition temperature, that is, the glass material has hardened, the pressure force is transmitted to the mold which can be cracked or even broken and sometimes, the glass material itself can be cracked.

No particular limitation is imparted to the pressing technique during molding. Since the glass material can be molded under a low pressure of up to 20 MPa, especially up to 1 MPa, the invention eliminates a need for special press means and enables molding by merely using a hand press or weight, for example. In the case of a weight, the mold is heated with the weight rested on the punch. Then the weight descends as the glass material lowers its viscosity. The completion of molding can be detected by the termination of downward displacement of the weight. Also, when a pressure force is applied by a press machine with a constant crosshead speed maintained, the completion of molding may be determined in terms of crosshead displacement or pressure increase.

FIGS. 2 to 5 illustrate exemplary pressure molding procedures. An apparatus for shaping a living tissue replacement by pressure molding includes a mold 2 and a punch 4. The mold 2 includes a molding cavity 21 and a bore 23 which receives the punch 4 and is connected for fluid communication to the cavity 21 through a sprue 22. The cavity 21 is of a dental crown shape in the illustrated examples. A frame 5 is an outer frame which is used when the mold 2 is cast. A buffer 6 lined inside the casting frame 5 is to accommodate expansion of the mold material. Often the casting frame 5 is an iron ring, and the buffer 6 is an asbestos ribbon. The molding cavity 21, sprue 22 and bore 23 are defined by a conventional lost wax process or the like. A block of glass material 3 is placed at the bottom of the bore 23 and compressed by the punch 4 in the arrow direction. Since the glass material has been heated to a predetermined temperature and thus has a low viscosity, the applied pressure causes the glass material to flow into the cavity 21 through the sprue 22 where it deforms faithfully to the cavity 21 to assume the dental crown shape.

Figure 2:
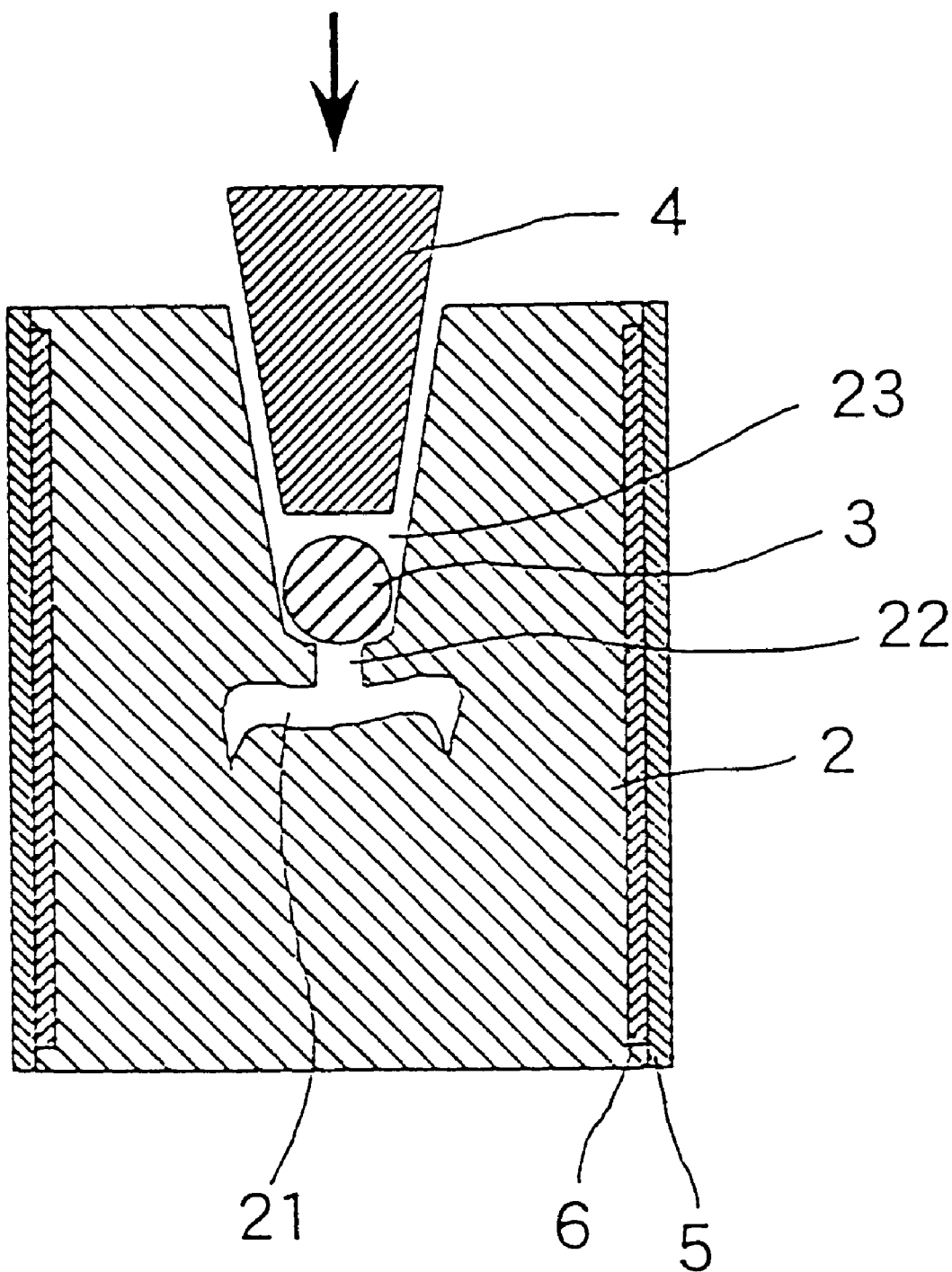
FIGS. 2 to 5 are schematic sectional views of molds showing different exemplary versions of pressure molding step.
Figure 3:
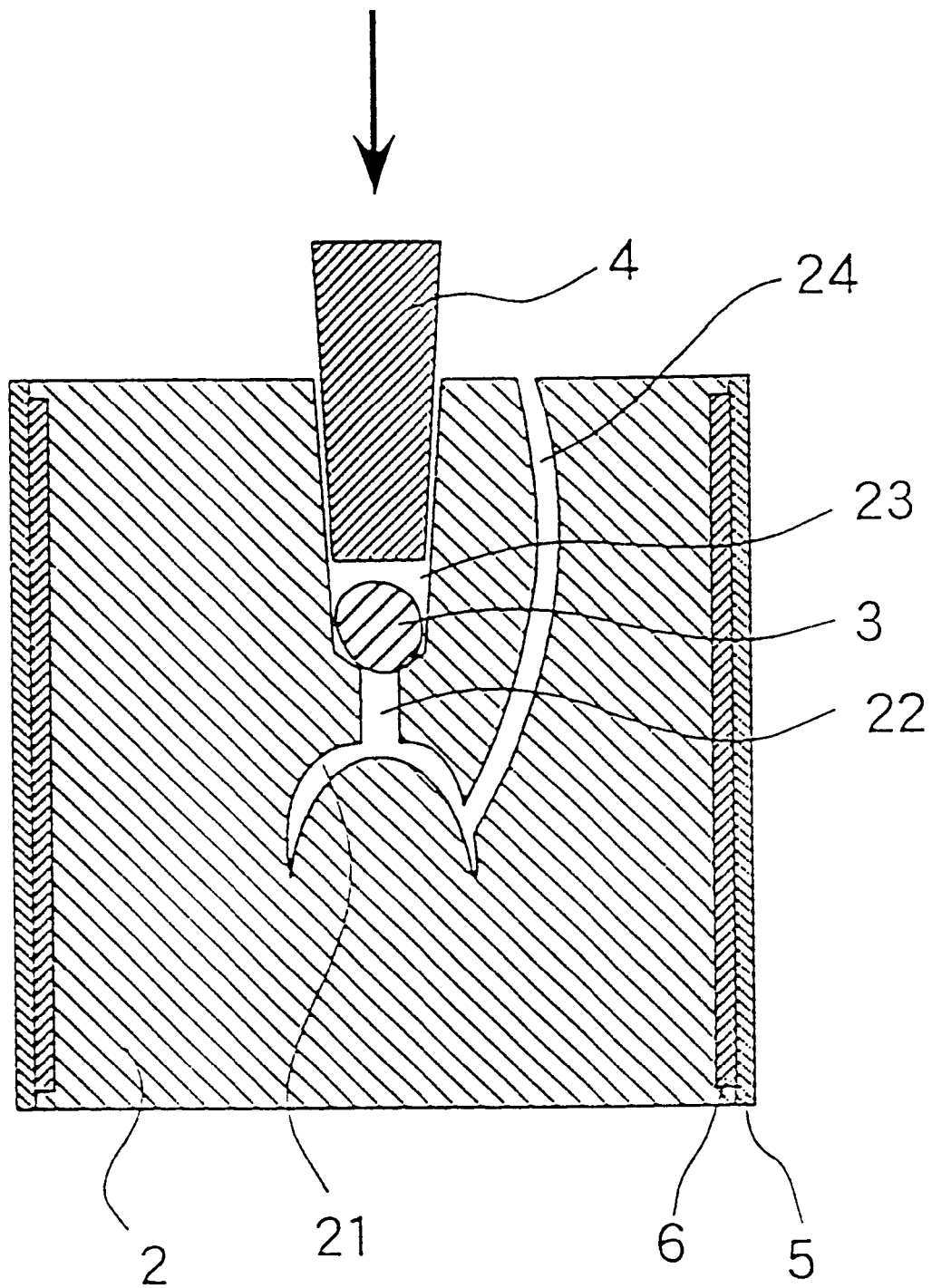

In the embodiments shown in FIGS. 2 and 3, the bore 23 has a tapered inner surface. The bore inner surface is inwardly tapered, preferably at a gradient of up to ⅕, more preferably up to ⅟15. In the preferred embodiment shown in FIG. 4, the bore 23 has a straight inner surface. The bore inner surface extends substantially parallel to the pressure application direction shown by the arrow. The bore with a slightly tapered or straight inner surface defines with a similarly tapered or straight punch 4 a minimal gap which is effective for preventing back flow of the softened glass material 3 therethrough. This saves the initial amount of glass material to be loaded. The bore 23 is generally circular in cross section (taken perpendicular to the pressure application direction) although it may also be ellipsoidal or polygonal.

Figure 4:
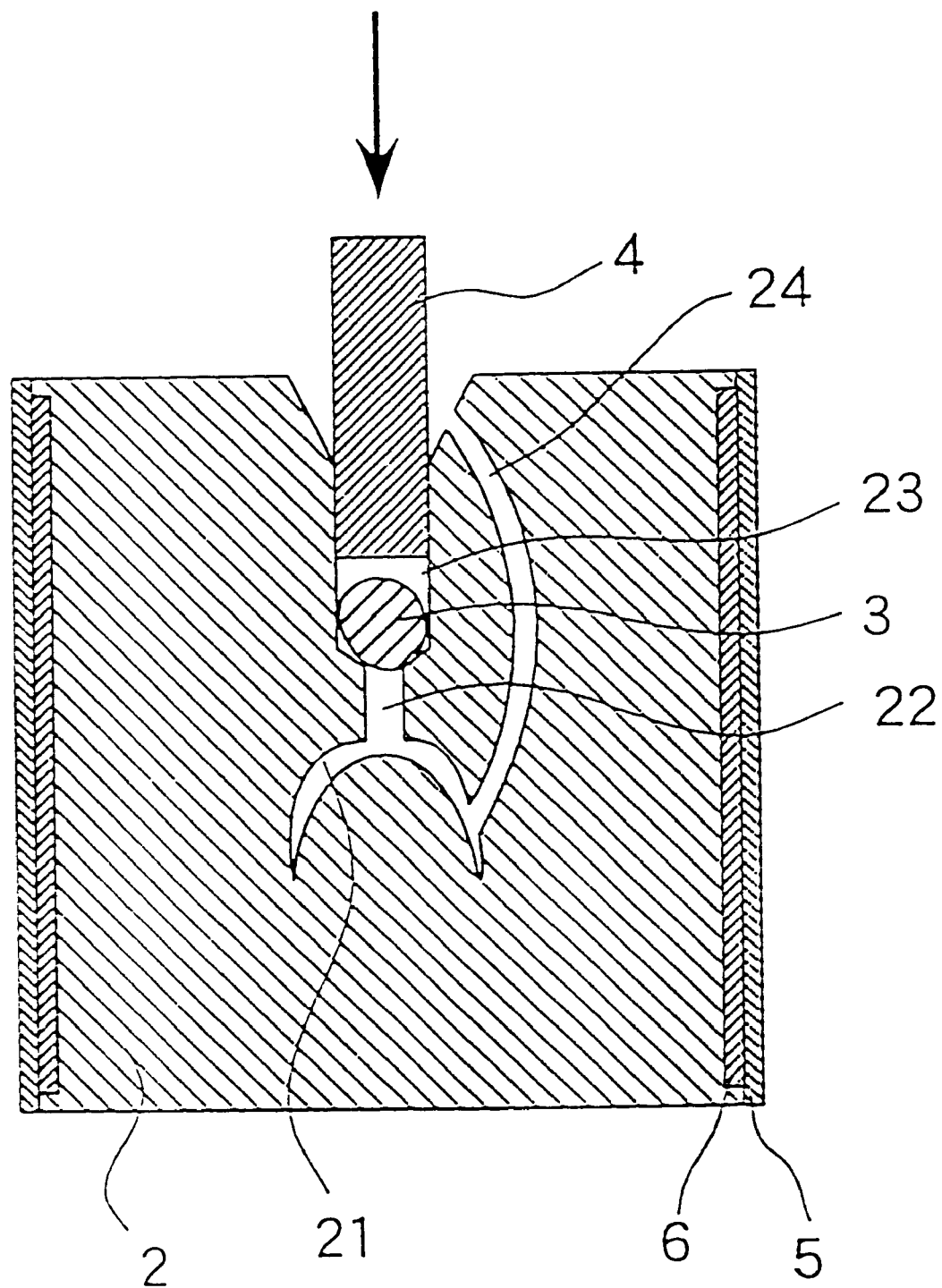
Figure 5:
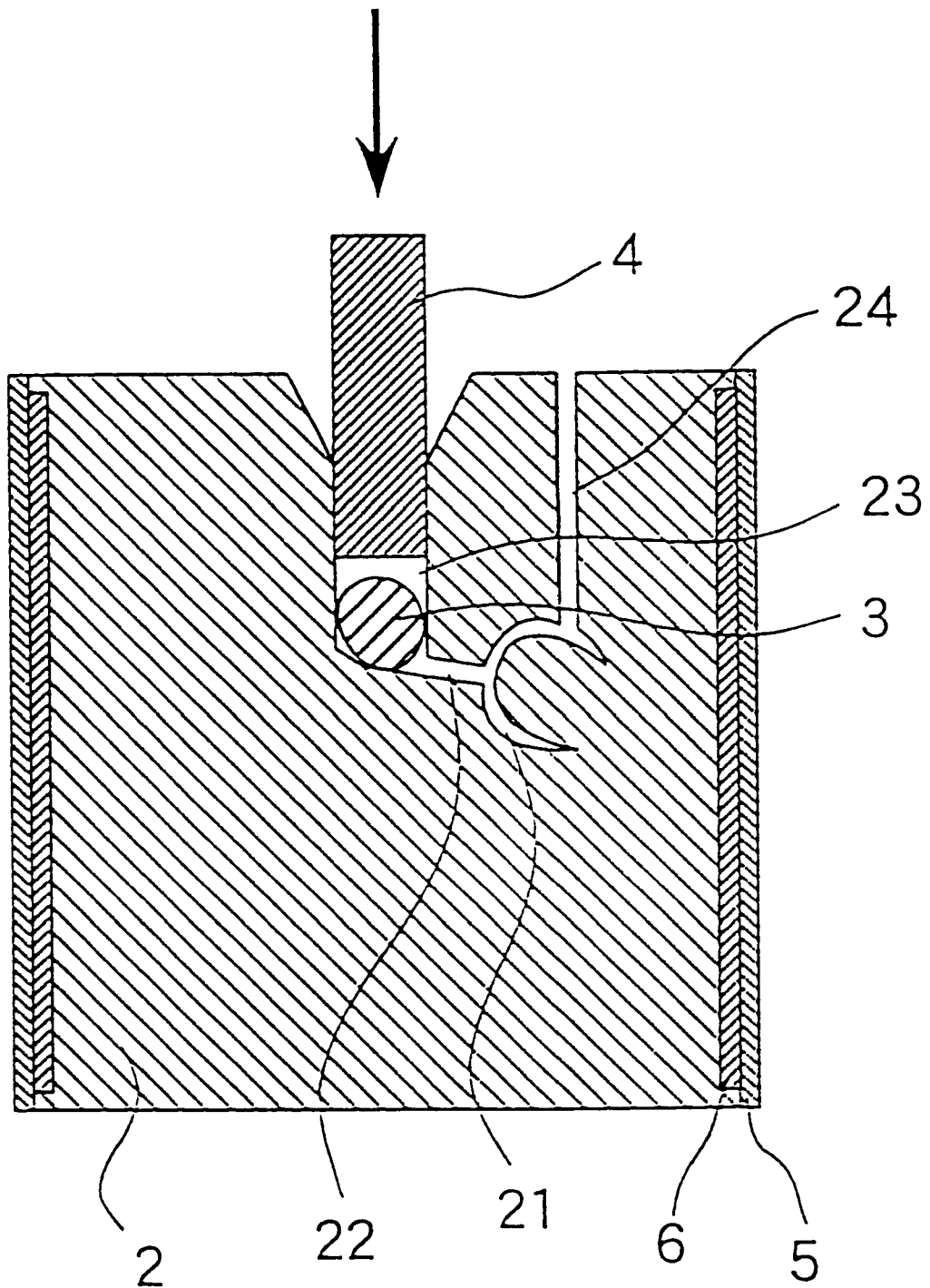

Preferably the mold 2 is provided with a vent or run-off path 24 connected in fluid communication between the molding cavity 21 and the exterior as shown in FIGS. 3 to 5. The vent 24 allows part of the glass material to run off upon pressure application, thereby facilitating to fill the cavity 21 with the glass material and to produce a molded part faithful to the cavity under a relatively low pressure. The vent 24 is also effective for preventing application of excess pressure to the mold upon pressure application, thus preventing the mold 2 from cracking. As a result, the percentage of deficient parts is drastically reduced. The diameter and cross-sectional shape of the vent 24 may be suitably determined depending on the volume and shape of the molding cavity 21. More than one vent 24 may be provided. Often the vent 24 is defined by a conventional lost wax process or the like. In the illustrated embodiments, the vent 24 opens to the exterior of the mold 2. Since conventional dental molds are well air permeable, it is unnecessary to discharge air in the molding cavity 21 through the vent 24. Then the vent 24 need not open to the exterior of the mold 2. The vent 24 is communicated to the mold exterior in the illustrated embodiments because such a through-vent is easier to define by a lost wax process.

Although the sprue 22 connecting the molding cavity 21 and the punch-receiving bore 23 is aligned with the pressure application direction shown by the arrow in the embodiments shown in FIGS. 2 to 4, the sprue 22 is preferably inclined with respect to the pressure application direction as shown in FIG. 5. The inclined sprue 22 facilitates to channel the glass material into the cavity 21 and to produce a molded part faithful to the cavity under a relatively low pressure and prevents the mold 2 from cracking upon pressure application. The angle of inclination relative to the pressure application direction is not particularly limited although it is desired that when the inlet and outlet of the sprue 22 are projected to a plane perpendicular to the pressure application direction, their projected images do not overlap. As long as the inlet and outlet of the sprue 22 are offset in this relationship, the sprue 22 need not be a straight one as shown in FIG. 5, with a curved sprue acceptable.

The sprue 22 preferably has a cross-sectional shape corresponding to the shape of the molding cavity 21. When it is desired to mold an artificial dental crown for the incisor as in the illustrated embodiment, the molding cavity 21 has a rectangular shape with high flatness in a cross section perpendicular to the sprue 22 and hence, the sprue 22 should also have a corresponding rectangular shape with a flatness of about 1:7 in cross section. Then a molded body of a shape highly faithful to the molding cavity 21 can be produced under a relatively low pressure. The sprue 22 need not have a constant cross-sectional area from the inlet to the outlet and may vary in area.

Figure 10:
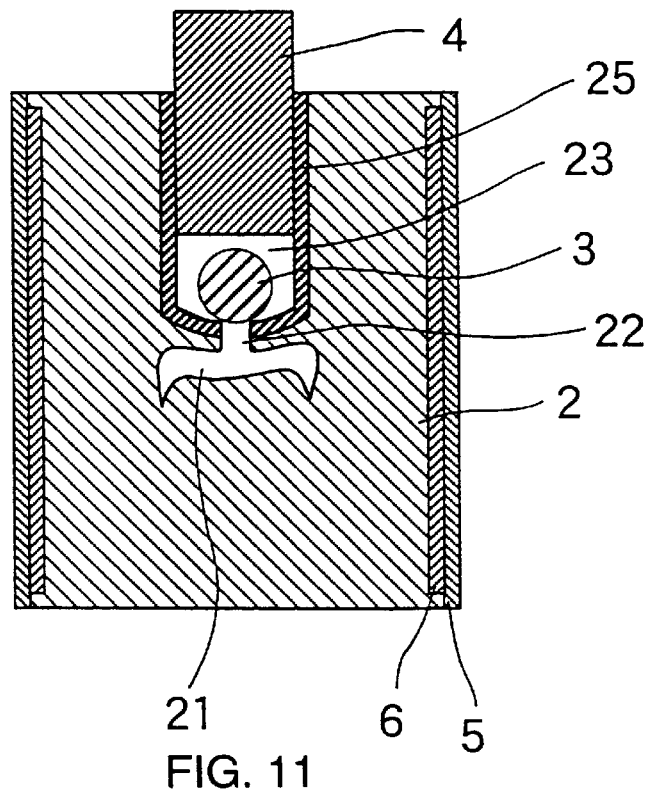
FIGS. 10, 11, and 12 are schematic sectional views of a mold including a bore having a high strength liner on its inner surface.
Figure 11:
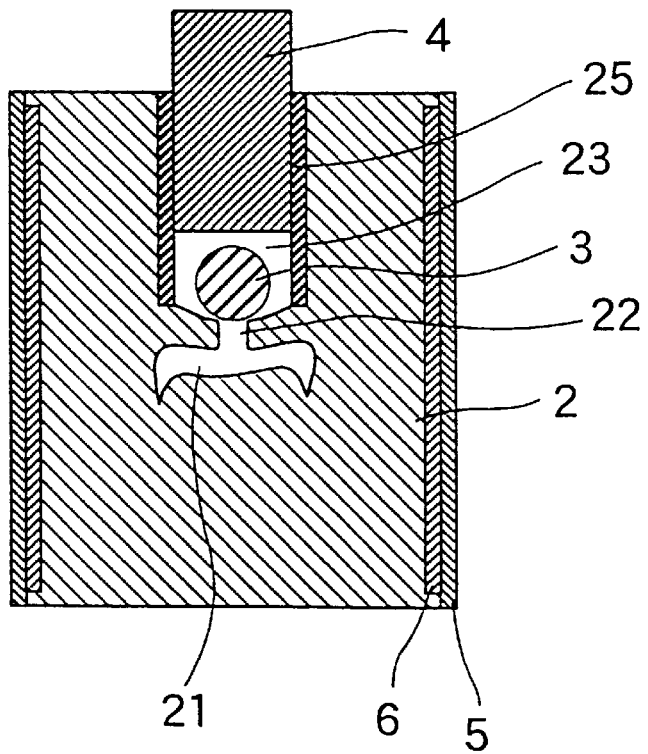

In a further preferred embodiment, the mold 2 includes a liner 25 which covers at least a portion of the inner surface of the punch-receiving bore 23 as shown in FIGS. 10 and 11. The liner 25 is made of a reinforcing or high strength material having a higher compression strength than the material of the mold 2. The bore 23 is lined with the high strength liner 25 at its inner surface for preventing rupture of the molded part. Since pressure is applied to the mold 2 during pressure molding, the mold 2 can be cracked. If the glass material penetrates into such cracks, there is a likelihood that the molding cavity 21 be short of the glass material. Still worse, if cracks are communicated to the cavity 21, the resulting molded part has burrs. Such cracking can be avoided by increasing the strength of the mold with a concomitant failure of the molded part upon withdrawal from the mold. This is because the molded part is generally withdrawn from the mold by applying an external force to the mold to form cracks therein and removing the mold material fragments. To destroy the high strength mold, a greater force must be applied to the mold so that the inside molded part can be damaged thereby. Then in the embodiments shown in FIGS. 10 and 11, the bore 23 is provided with the high strength liner 25 on the inner surface and the mold 2 itself is made of a material having relatively low compression strength, which not only prevents the mold from cracking under the molding pressure, but also ensures that the mold is readily destroyed without causing damage to the inside molded part upon withdrawal of the molded part from the mold.

Figure 12:
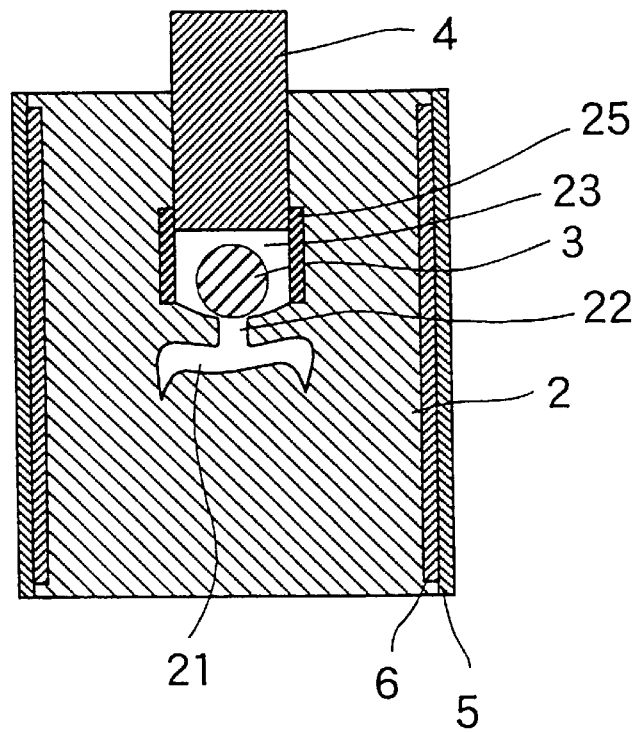

Although the high strength liner 25 is preferably extended over the entire inner surface of the bore 23 as shown in FIG. 10, it is only required that the liner 25 cover a portion of the bore inner surface, especially that portion of the bore inner surface which comes in contact with the glass material 3 during pressure molding. Since it is rather difficult and expensive to apply high strength material to the entire bore inner surface to form the liner 25 shown in FIG. 10, it is acceptable that the high strength material or liner be not applied near the bottom of the bore 23 as shown in FIGS. 11 and 12.

The high strength liner 25 is generally about 0.1 to about 3 mm thick although the thickness is not critical and may be suitably determined by taking into account the type of high strength material and molding pressure.

Figure 13:
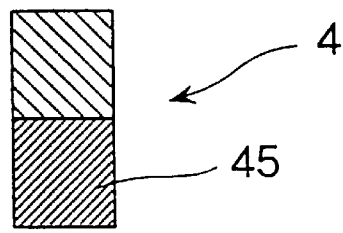
FIGS. 13(*a*), 13(*b*) and 13(*c*) are cross-sectional views of a punch partially formed of a high strength material.
Figure 13:
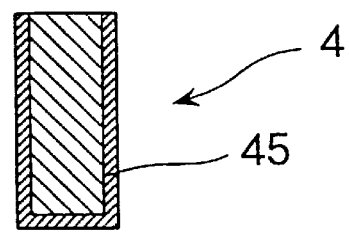
Figure 13:
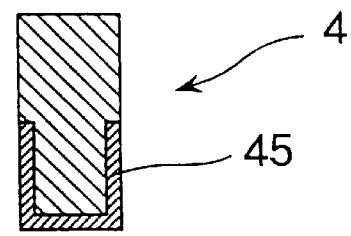

The punch 4 receives only compression stress in a substantial sense. Then even when the punch 4 is made of a material having relatively low compression strength, its failure is less probable. However, it is preferred that the punch 4 is at least partially formed of a reinforcing or high strength material 45 having higher compression strength than the material of the mold 2 as shown in FIGS. 13(a), 13(b) and 13(c). The high strength material or cover 45 prevents the punch 4 from such failure as cracks and fracture. The reinforcement or cover 45 of high strength material forms or covers at least a portion of the surface of the punch 4 opposed to the bore inner surface, especially that portion of the punch surface which comes in contact with the glass material 3 during pressure molding. Since there is a tendency that some glass deposits remain on the punch 4 after molding, it is a common practice to replace the punch 4 by a new one on every molding operation. Then the embodiment wherein only a portion of the punch 4 is made of the high strength material as shown in FIG. 13 is cost effective because the punch can be manufactured at a lower cost by reducing the amount of the high strength material which is expensive than the low strength investment materials. The high strength cover 45 in the embodiments of FIGS. 13(b) and 13(c) may have a thickness similar to that of the liner 25 associated with the bore 23.

The material of which the mold 2 is made preferably has a compression strength of up to 20 MPa, more preferably up to 15 MPa and preferably at least 2 MPa, more preferably at least 4 MPa at the end of pressure molding. If the compression strength of the mold material is too high, the probability of molded part failure would become high for the above-mentioned reason. If the compression strength of the mold material is too low, the mold would be broken during molding even when the high strength liner is provided.

The compression strength of the mold material is defined herein as that after compression molding because the mold is concurrently heated during pressure molding and the compression strength depends on this heating. It is possible to facilitate withdrawal of the molded part from the mold by immersing the mold in water for softening and in this case, the compression strength is that of the mold which has been immersed in water.

Also preferably the high strength material for the liner 25 (FIGS. 10–12) and the cover 45 (FIG. 13) has a compression strength of at least 15 MPa, more preferably at least 30 MPa. With a compression strength below the limit, provision of the reinforcing material would be meaningless. No upper limit need be imposed on the compression strength of the reinforcing material. Often a material having a compression strength of up to 2,000 MPa is preferably used for availability and ease of shaping.

The compression strength used herein is measured according to JIS R 1608 when the mold material and reinforcing material are ceramics. More particularly, five cylindrical samples of 12.5 mm in diameter and 5 mm height are molded from the material and measured for compression strength at a crosshead speed of 0.5 mm/min. For a metallic reinforcing material, the compression strength is given as the value at which an object on test is broken when the same compression strength measuring procedure as used for the ceramics is carried out.

The material having relatively low compression strength of which the mold 2 is made may be suitably selected from dental investment materials, for example, cristobalite and phosphate system cristobalites such as calcium phosphate cristobalite as well as gypsum, with the cristobalite being preferred. Cristobalite may be softened, further softened by immersing in water, or smoothed on surface. The high strength material for the liner 25 or reinforcement 45 is not particularly limited and may be suitably selected by taking into account its relationship to the compression strength of the mold material, preferably from metal and ceramic materials. Ceramic materials are especially preferred because heat during pressure molding can cause metals to react with the glass material to undesirably color the glass material. Preferred examples of the metal are stainless steel and iron while preferred examples of the ceramic include alumina, silicon carbide, zirconia, and zeolite. Ceramic mixtures such as mixtures of various porcelains and refractories (e.g., feldspar-quartz-kaolin systems) are also preferred. Further phosphate system cristobalites, dental refractories and gypsum are acceptable.

Preferred investment compounds are of cristobalite and gypsum systems, such as OK Powder commercially available from Shofu K.K. As opposed to other castable ceramics, investment compounds of cristobalite and gypsum systems, which ensure facile removal of molded parts and improved surface properties can be used because the molding temperature is relatively low.

Any desired method may be used to form the liner 25 and reinforcement or cover 45 of high strength material although the following method is often used.

Figure 14:
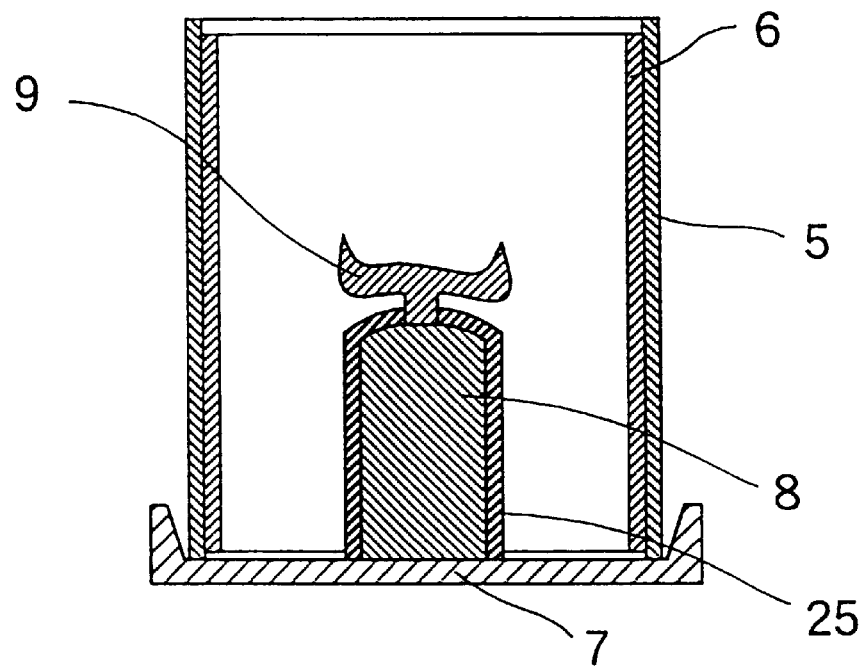
FIG. 14 is a cross-sectional view illustrating how to provide the bore with a high strength liner.

FIG. 14 illustrates how to form the mold 2 by a lost wax process. The casting frame 5 and buffer 6 are rested on a support 7. A shape 8 of silicone rubber or the like for forming the punch-receiving bore is placed within the frame 5. A high strength material is applied to the surface of the shape 8 to form the liner 25. On the shape 8 is located a wax shape 9 for forming the sprue and cavity. In this state, a mold material such as an investment compound is cast into the frame 5 followed by ordinary steps of a conventional lost wax process.

Figure 15:
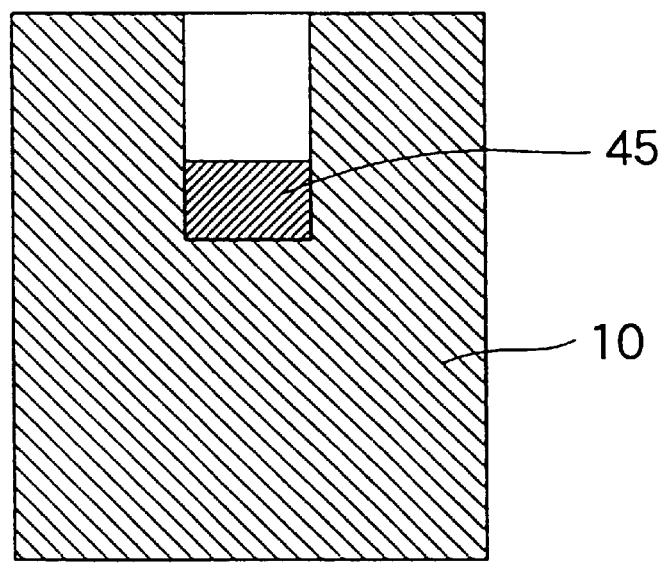
FIG. 15 is a cross-sectional view illustrating how to prepare a punch partially formed of a high strength material.

The punch 4 including a lower portion in the form of the high strength material reinforcement 45 shown in FIG. 13(a) is prepared, as shown in FIG. 15, by placing a high strength material 45 in a cavity of a punch-forming mold 10 of silicone rubber or the like, casting a punch material such as an investment compound thereon, and removing the mold 10.

After the glass material is pressure molded by the living tissue replacement molding apparatus mentioned above, the molded part is allowed to cool down inside or outside the furnace. If desired, the molded part is slowly cooled at a controlled rate. The molded part can be taken out of the mold by an ordinary technique commonly employed by the dentist or dental technician.

Crystallization treatment is made on the molded part of glass material by holding the molded part approximately at the crystallization temperature, preferably in the range between the crystallization temperature minus 200° C., more preferably the crystallization temperature minus 100° C. and the crystallization temperature plus 50° C. (Tx−200° C.≦T≦Tx+50° C.). The holding time is not critical and is suitably determined such that a desired crystallinity may be obtained. Often the holding time is within 10 hours, preferably within 3 hours. It is also acceptable to omit temperature holding, that is, to start cooling immediately after the predetermined temperature is reached.

Where crystallization treatment follows the pressure molding step, it is recommended to subject the molded part to crystallization treatment without cooling because the overall process becomes efficient.

Crystallization can be done without taking the molded part out of the investment compound after molding. In contrast, conventional castable ceramics have a likelihood that the glass be broken because the molded part must be removed prior to crystallization and if crystallization is done without removal, the molded part be cracked due to differential expansion from the investment compound. The present invention enables crystallization within the mold without cracking because of minimal thermal expansion.

The molded part after crystallization has a structure wherein crystalline phase is dispersed in the vitreous matrix. The proportion of crystalline phase, that is, crystallinity is not particularly limited although it is preferably at least 10% by volume, more preferably 20 to 100% by volume. A glass material with too low crystallinity would be inadequate as the dental crown because of insufficient mechanical strength and high clarity. Also undesirably, when a projection corresponding to the sprue is removed, the fracture surface would become sharp. It is to be noted such a projection corresponding to the sprue is removed by abrasion.

Figure 7:
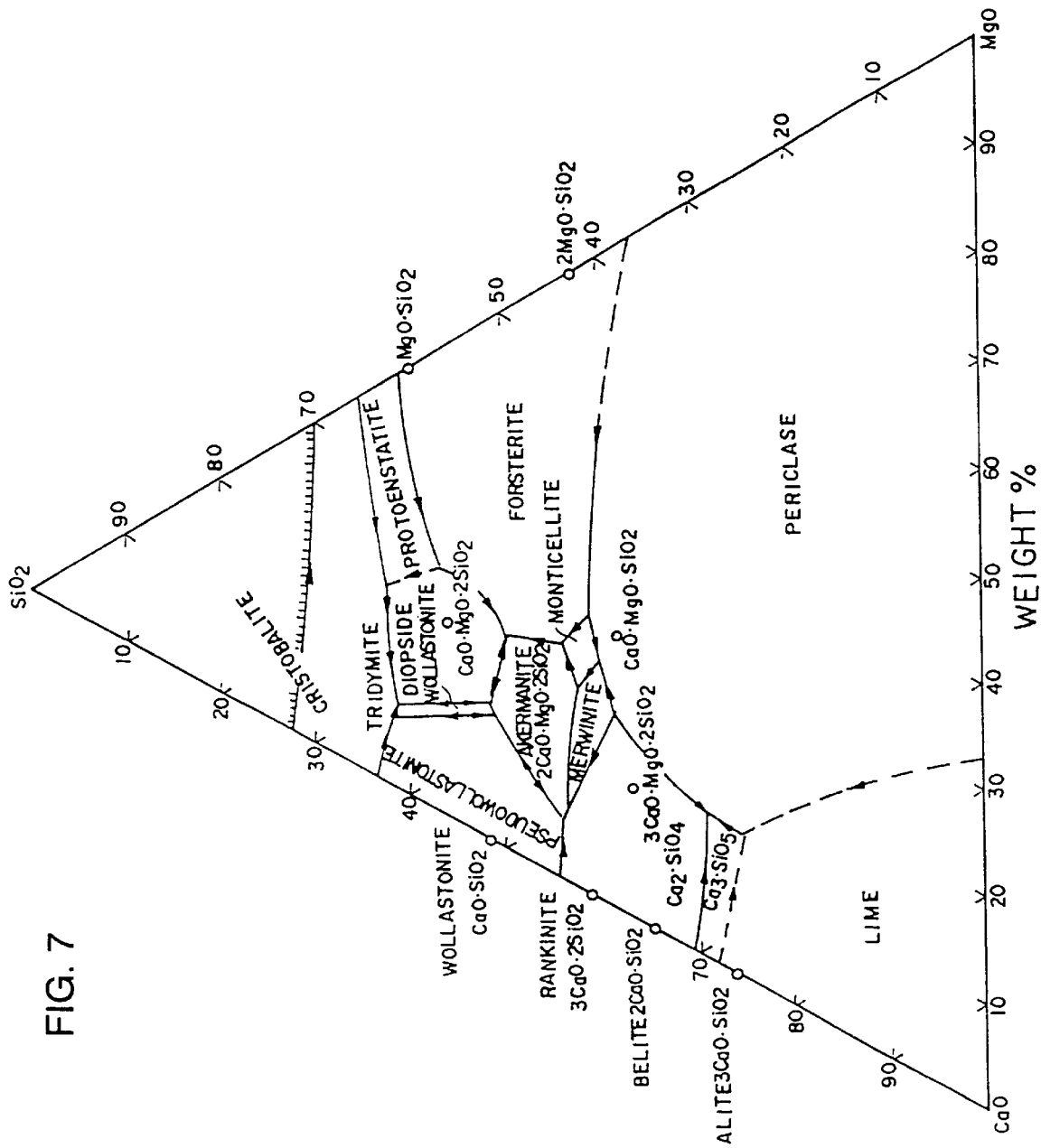
FIG. 7 is a ternary diagram of $SiO_2$—$CaO$—$MgO$ system for explaining the composition of preferred ceramic material.

The resulting crystals are shown in the ternary phase diagram of FIG. 7. In a preferred range of composition according to the present invention, there is mainly created diopside: $(Ca,Mg)O—MgO—2SiO_2$, preferably $CaO—MgO—2SiO_2$. In a more preferred range of composition, there is substantially solely created diopside. Diopside preferably occupies at least 30% by volume, more preferably at least 70% by volume, most preferably at least 80% by volume of the entire crystalline matter. Besides diopside there are created other crystals including wollastonite: $\beta—(Ca,Mg)O—SiO_2$, especially $CaO—SiO_2$, alite: $3CaO—SiO$, belite: $2CaO—SiO_2$, akermanite: $2CaO—MgO—2SiO_2$, monticellite: $CaO—MgO—SiO_2$, forsterite: $2(Mg,Ca)O—SiO_2$, protoenstatite: $(Mg,Ca)O—SiO_2$, and tridymite: $SiO_2$. Preferred among these are akermanite and/or monticellite.

The crystallinity used herein can be determined by a peak separation technique using an X-ray diffraction chart. In an X-ray diffraction chart of crystallized glass having crystals dispersed in a vitreous matrix, there appear a halo indicative of the presence of vitreous matter and inherent peaks corresponding to a particular crystalline matter. The peak separation technique determines an integral intensity as a sum of only peak areas and an overall integral intensity as a sum of peak and halo areas and divides the former by the latter to calculate a crystallinity.

At the end of crystallization, the average grain size generally ranges from about 0.001 to about 100 μm, preferably up to 1 μm, more preferably up to 0.5 μm. It is difficult to provide a grain size smaller than this range whereas high strength would not be expected from a too large grain size. The grain size is determined by measuring the area of each grain in a photomicrograph under a scanning electron microscope (SEM) and calculating the diameter of a circle corresponding to the area.

In the present invention, the glass transition temperature, softening point, crystallization temperature and nucleation temperature may be determined by differential thermal analysis and measurement of a coefficient of thermal expansion. It is to be noted that since the glass transition temperature, softening point, and crystallization temperature do not substantially alter after nucleation, the heating temperature used for the pressure molding of a previously nucleated glass material may be determined on the basis of the glass transition temperature and softening point of a non-nucleated glass material. The same applies to those glass materials which have been crystallized such that pressure molding may be done under a pressure of less than 20 MPa as shown in FIGS. 1(d) and 1(e).

Living tissue replacements such as artificial dental crowns may be directly prepared by pressure molding of glass material as mentioned above. It is also possible that the molded part resulting from pressure molding be machined prior to completion of a living tissue replacement. The machining step is advantageous in producing a living tissue replacement of complex shape to which a mold cavity can be precisely molded with difficulty or in producing a living tissue replacement which requires very high dimensional precision. If the molded part has a shape and size approximate to the final living tissue replacement, machining can be completed within a short time and the waste of glass material can be reduced. Alternatively, it is possible to directly machine a block of glass material without pressure molding. There may be used any of machining techniques including machining using drills of high hardness material such as diamond and carborundum, lathes and the like.

Where the living tissue replacement is an artificial dental crown, it is generally stained after crystallization.

Figure 6:
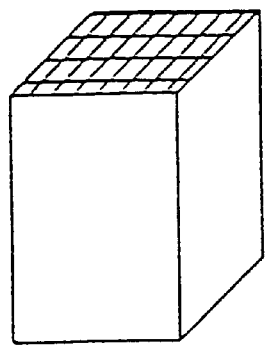
FIG. 6 illustrates examples of the living tissue replacement according to the invention, FIG. 6(*a*) is an artificial vertebra body, FIG. 6(*b*) is an artificial intervertebral body, FIG. 6(*c*) is an artificial iliac bone, FIG. 6(*d*) is an artificial air tube, and FIG. 6(*e*) is a bone screw.
Figure 6:
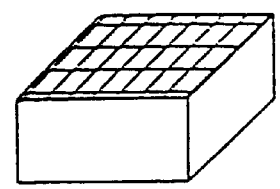
Figure 6:
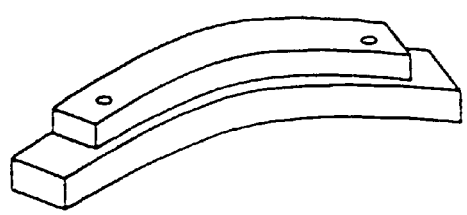
Figure 6:
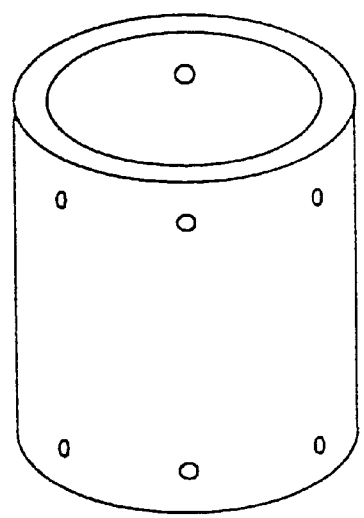
Figure 6:
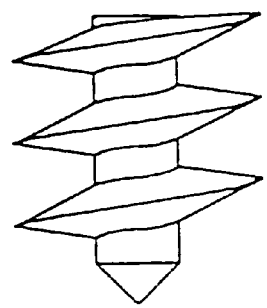

Although the invention has been described as being applied to artificial dental crowns, the invention is equally applicable to other living tissue replacements, for example, artificial bones such as ossiculum, bone screws, percuteneous terminals, blood vessels, and air tubes. Such examples of the living tissue replacement are illustrated in FIG. 6. FIG. 6(a) is an artificial vertebra body, FIG. 6(b) is an artificial intervertebral body, FIG. 6(c) is an artificial iliac bone, FIG. 6(d) is an artificial air tube, and FIG. 6(e) is a bone screw.

EXAMPLE

Examples of the present invention are given below by way of illustration and not by way of limitation.

Examples 1–10 & Comparative Examples 1–3

Glass Material

Guaranteed reagents $CaCO_3$, $SiO_2$, and MgO (available from Kanto Chemical K.K.) were weighed as shown in Table 1 and milled in a vibratory mill with zirconia balls for one hour. Each mixture was placed in a 30-cc platinum crucible and heated in an electric furnace model SuperBurn (manufactured by Motoyama K.K.) for one hour to form a molten glass. The melting temperature is shown in Table 1.

The molten glass was cast into a dental investment material Cosmotec Vest (manufactured by GC K.K.) for cooling and annealed at 750° C., obtaining a glass material. Some of the thus prepared glass material samples had a metal or metal compound added thereto as shown in Table 1. The content of the additive is expressed in percent by weight based on the total of $CaO+SiO_2+MgO=100\%$ by weight.

These glass material samples as prepared were measured for melting temperature, nucleation temperature and crystallization temperature (Tx) by differential thermal analysis and for glass transition temperature (Tg) and softening point (Td) by a thermal expansion/contraction test. The differential thermal analysis was carried out by crushing the glass material in an alumina mortar, weighing a 65-mg portion therefrom, and heating the sample at a rate of 10° C./min. by a differential thermal analysis meter (manufactured by Mac Science Co.). The thermal expansion/contraction test used a specimen of 3×4×35 mm having surfaces mirror finished with diamond paste and a thermal expansion/contraction meter (manufactured by Shimazu Mfg. K.K.) operating at a heating rate of 5° C./min. The results are shown in Table 1. It is to be noted that the glass material samples were also measured for melting point by differential thermal analysis to find that all the samples had a melting point of higher than 1,400° C.

Nucleation Treatment

Some of the glass material samples were subject to nucleation treatment by heating at the nucleation temperature shown in Table 1 for 8 hours in an electric furnace model SuperBurn (manufactured by Motoyama K.K.). Whether or not the samples were subject to nucleation treatment is shown in Table 1.

Pressure Molding

A mold and punch for pressure molding were prepared from a dental investment material Cosmotec Vest (manufactured by GC K.K.) having a compression strength of about 50 MPa. A frustoconical block (height 5 mm, maximum diameter 5 mm, minimum diameter 4 mm) of the glass material was placed in the bore of the mold, which was heated at a rate of 20° C./min. in a split electric furnace SS-1700 (manufactured by Nems K.K.). After a soaking time of 10 minutes passed, the glass material was pressure molded in the furnace. By means of a strength tester Instron 1350 (manufactured by Instron) with a constant crosshead speed of 0.5 mm/min., a pressure was applied to the glass material in its axial direction to achieve molding within a maximum displacement of 3 mm. Provided that the distortion of glass material corresponds to the displacement of the crosshead, a load-distortion curve was recorded. The applied pressure was calculated according to the equation:

$$S = p/A$$

wherein p is the load, A is the minimum cross-sectional area of the glass material before deformation, and S is the applied pressure. The molding pressure reported in Table 1 implies the applied pressure to effect a distortion of 25%, the distortion being a deformation of glass material divided by the height of glass material before deformation.

Figure 9:
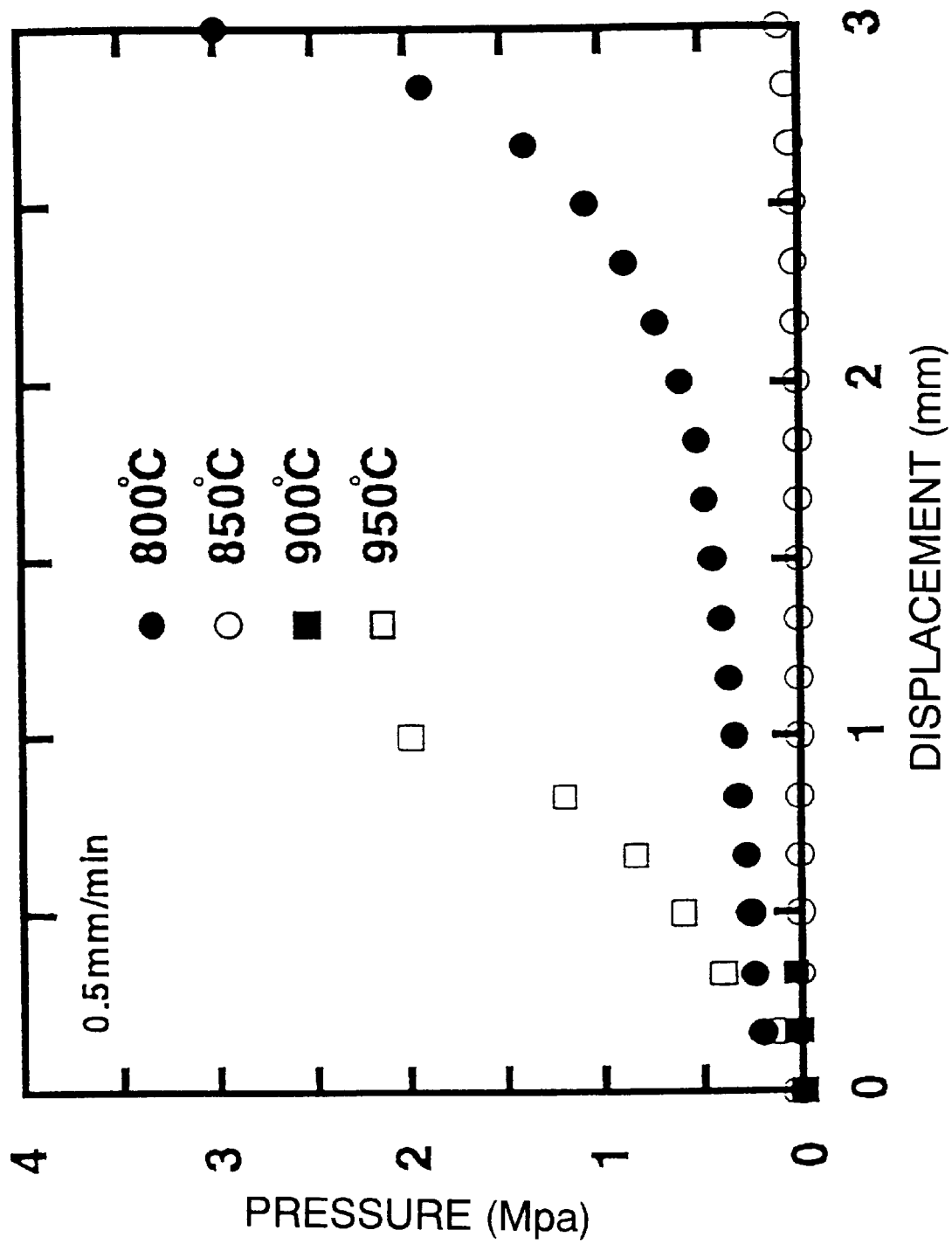

The relationship of applied pressure and displacement during pressure molding in Examples 2–3 and Comparative Examples 1–2 is illustrated in FIG. 9. It is seen that at 800° C. and 850° C. which are higher than the softening point (782° C.) and lower than the crystallization temperature (870° C.), deformation took place under a pressure of lower than 3 MPa (about 30 g/cm$^2$) and lower than 0.1 MPa (about 1 g/cm$^2$), respectively, even at a displacement of about 3 mm (corresponding to a distortion of about 60%). At temperatures of 900° C. and 950° C., the specimens were ruptured on the way of increasing the applied pressure. The ruptured fragments were whitened and had a crystallinity of more than 60% by volume. This implies that pressure molding at 900° C. or higher induced excess crystallization which inhibited sufficient deformation.

Pressure Molding Outside the Furnace

The glass material was prepared by the same procedure as Example 3, subject to nucleation treatment, and then molded by the following procedure.

In an electric furnace KDFVR7 (manufactured by Ring Furnace) set at 850° C., a pressure molding mold and punch assembly loaded with the glass material was placed and held at the temperature for 10 minutes. Immediately after the

TABLE 1

Glass-forming raw material composition

| | Base composition (total 100 wt %) | | | |
|---|---|---|---|---|
| | CaO | SiO$_2$ | MgO | Additive (wt % based on base composition) |
| E 1 | 26 | 55.8 | 18.2 | |
| E 2 | 26 | 55.8 | 18.2 | |
| E 3 | 26 | 55.8 | 18.2 | |
| CE 1 | 26 | 55.8 | 18.2 | |
| CE 2 | 26 | 55.8 | 18.2 | |
| E 4 | 26 | 55.8 | 18.2 | Ag (0.01) |
| E 5 | 26 | 55.8 | 18.2 | Au (0.01) + Fe$_2$O$_3$ (0.2) + ZrO$_2$ (3) |
| E 6 | 26 | 55.8 | 18.2 | Ag (0.01) + Fe$_2$O$_3$ (0.2) + ZrO$_2$ (3) + CeO$_2$ (0.05) + TiO$_2$ (10) |
| E 7 | 32 | 51.5 | 16.5 | Ag (0.01) + CeO$_2$ (0.5) |
| E 8 | 22.6 | 69.4 | 8 | Au (0.01) + TiO$_2$ (1.0) + CeO$_2$ (0.5) |
| E 9 | 40 | 45 | 15 | Au (0.01) + CeO$_2$ (0.5) |
| E 10 | 20.3 | 55.2 | 24.5 | Au (0.01) + Fe$_2$O$_3$ (0.2) |
| CE 3 | 45.5 | 50 | 4.5 | Au (0.005) + CeO$_2$ (0.1) |

| | Melting temp. (° C.) | Nucleation Temp. (° C.) | Nucleation treatment | Tg (° C.) | Td (° C.) | Tx (° C.) | Molding temp. (° C.) | Crystallinity after molding (%) | Molding pressure (MPa) |
|---|---|---|---|---|---|---|---|---|---|
| E 1 | 1450 | 550 | none | 732 | 782 | 870 | 750 | 0 | 15 |
| E 2 | 1450 | 550 | none | 732 | 782 | 870 | 800 | 0 | 0.3 |
| E 3 | 1450 | 550 | none | 732 | 782 | 870 | 850 | 0 | <0.01 |
| CE 1 | 1450 | 550 | none | 732 | 782 | 870 | 900 | 60 | rupture |
| CE 2 | 1450 | 550 | none | 732 | 782 | 870 | 950 | 80 | rupture |
| E 4 | 1450 | 550 | treated | 732 | 782 | 870 | 850 | 0 | <0.01 |
| E 5 | 1450 | 500 | treated | 732 | 782 | 870 | 850 | 0 | <0.01 |
| E 6 | 1450 | 500 | treated | 740 | 782 | 870 | 850 | 0 | <0.01 |
| E 7 | 1450 | 500 | treated | 730 | 805 | 860 | 830 | 0 | <0.01 |
| E 8 | 1450 | 500 | treated | 725 | 780 | 840 | 800 | 0 | <0.01 |
| E 9 | 1450 | 500 | treated | 766 | 810 | 880 | 900 | 6 | <0.01 |
| E 10 | 1550 | 500 | treated | 730 | 770 | 840 | 800 | 0 | <0.01 |
| CE 3 | 1500 | 500 | treated | 790 | 850 | 1050 | 900 | 50 | rupture |

The glass materials of Examples 1–3 and Comparative Examples 1–2 had a coefficient of thermal expansion of 5.97×10$^{-6}$/°C. in the temperature range between 400° C. and 700° C.

Figure 8:
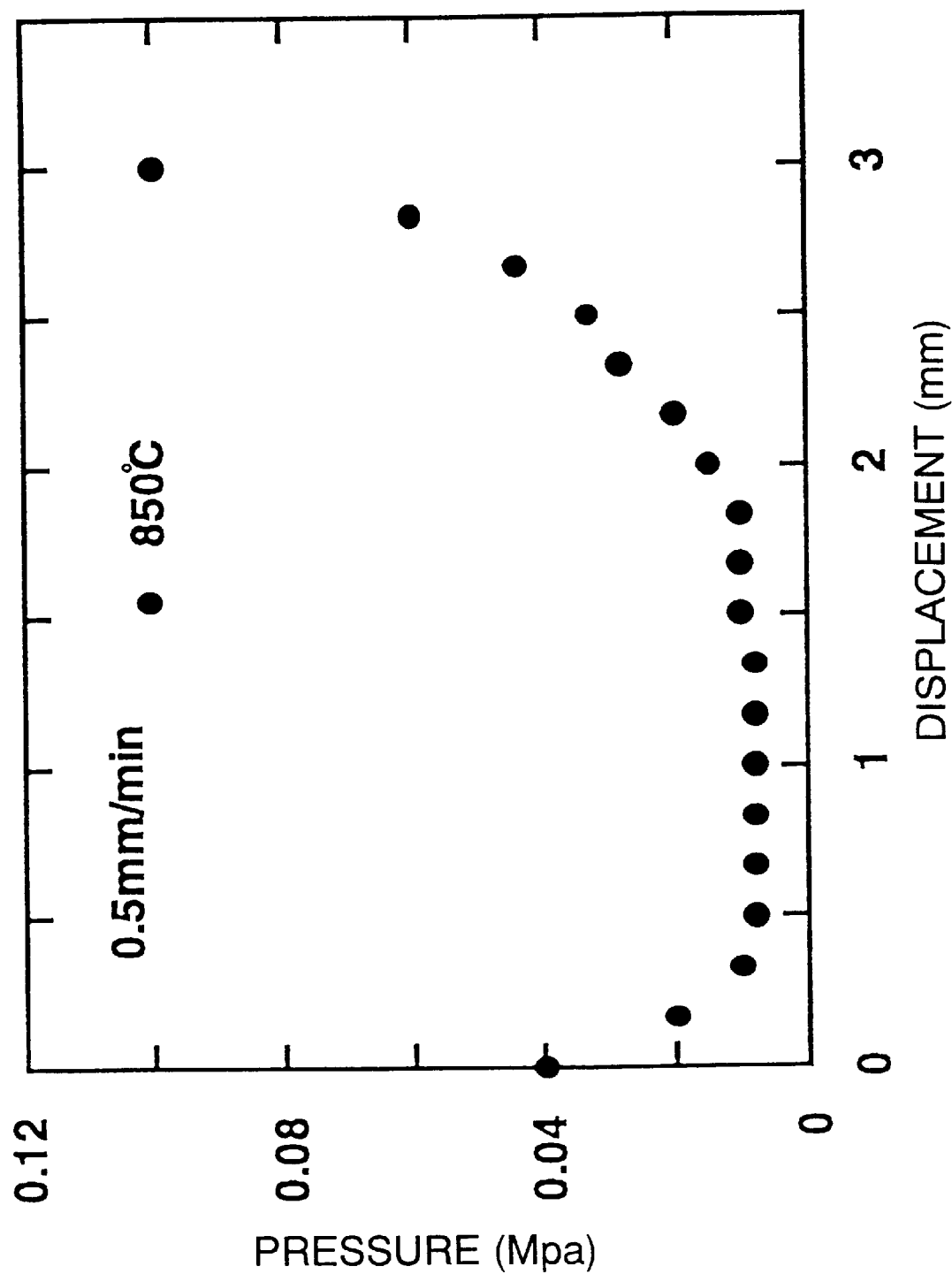
FIGS. 8 and 9 are graphs showing a distortion of glass material versus applied pressure.

The relationship of applied pressure and displacement during pressure molding in Example 3 is illustrated in FIG. 8. It is seen that deformation took place under a pressure of 0.008 MPa (about 80 g/cm$^2$) to 0.04 MPa (about 400 g/cm$^2$) until a displacement of 2 mm was reached.

assembly was taken out of the furnace, that is, before the temperature of the glass material began lowering, pressure was applied to the glass material by means of a press machine Shot Cure 2, Jiyo No. 52 (manufactured by Towa Giken K.K.). The pressure necessary for molding was the same as in Example 3.

Casting

Glass material was prepared as in Example 5 and molded by the following procedure.

In an electric furnace model SuperBurn (manufactured by Motoyama K.K.) operating at 1,450° C. was placed a mold and punch assembly loaded with the glass material. The glass material was melted by heating for 10 minutes. Immediately after the assembly was taken out of the furnace, that is, before the temperature of the glass material began lowering, pressure was applied to the molten glass material by means of a press machine Shot Cure 2, Shiyo No. 52 (manufactured by Towa Giken K.K.).

In this procedure, the glass reacted with the mold and the molten glass flowed back and did not fill the mold cavity to its extremity. Bubbles and cracks were observed in the molded part. Due to substantial shrinkage upon cooling, the part largely deviated from the desired dimensions.

After molding or casting, the part was subject to nucleation treatment and crystallization treatment, resulting in insufficient nucleation and non-uniform crystallization. Although the molded part prepared in Example 5 was tinted to a desired yellow color at the end of crystallization, the cast part did not possess the desired color, but a deeper color despite the same composition.

Examples 11–20 & Comparative Example 4

Each of glass materials as shown in Table 2 was heat treated in an electric furnace KDFVR7 (manufactured by Ring Furnace) for crystallization, obtaining a test specimen. The heating rate was 5° C./min. while the holding temperature and time are shown in Table 2. Examples 19–20 used the glass material which had the same composition as Example 5, but had not been nucleated. Precipitated phases of diopside (D) and akermanite (A) were identified by powder X-ray diffractometry analyzer XD-D1 (manufactured by Shimazu Mfg. K.K.).

The specimens were measured for flexural strength. The specimens were of the same dimensions as used for the thermal expansion/contraction test and had a similarly mirror finished surface. The flexural strength was measured by a three-point bend test using a strength tester ServoPulser EHF-F1 (manufactured by Shimazu Mfg. K.K.) at a crosshead speed of 0.5 mm/min. and a span of 15 mm. The number of test specimens was 5 for each lot. For comparison purposes, the glass material which had the same composition as Example 1, but was not crystallized (Comparative Example 4) was also measured for flexural strength. The results are shown in Table 2.

TABLE 2

| | | Crystallization | | Flexural | | |
|---|---|---|---|---|---|---|
| | Glass material | Temp. (° C.) | Time (hr.) | strength (MPa) | Precipitated phase | Outer appearance |
| CE 4 | E 1* | — | — | 120 | — | clear |
| E 11 | E 1* | 870 | 6.0 | 300 | diopside | white |
| E 12 | E 4 | 870 | 0.5 | 300 | diopside | white |
| E 13 | E 5 | 870 | 1.0 | 300 | diopside | yellow** |
| E 14 | E 6 | 870 | 1.0 | 300 | diopside | yellow** |
| E 15 | E 7 | 860 | 0.1 | 280 | diopside | yellow** |
| E 16 | E 8 | 840 | 0.5 | 250 | diopside | yellow** |
| E 17 | E 9 | 880 | 0.5 | 200 | diopside/akermanite | yellow** |
| E 18 | E 10 | 840 | 0.5 | 250 | diopside | yellow** |
| E 19 | E 5* | 890 | 5.0 | 300 | diopside | yellow** |
| E 20 | E 5* | 870 | 10.0 | 300 | diopside | yellow** |

*The glass materials used in CE 4, E 11, E 19, and E 20 had not been nucleated.
**natural tooth color As seen from Table 2, Examples 11, 19 and 20 which had not been nucleated required a substantially extended time for crystallization. The crystallized materials of these examples had a crystallinity of 30 to 50% by volume. In Example 17, diopside occupied 50% by volume of the precipitated phase.

Example 21

The procedure of Example 13 was repeated except that two blocks of glass material were placed in the bore upon pressure molding. Some voids were left in the molded part.

Comparative Example 5

The procedure of Example 13 was repeated except that the glass material used was a 200-mesh under powder. Many voids were left in the molded part.

Comparative Example 6

A glass material was prepared by melting a mixture of 24.8% CaO, 16.9% MgO, 16.3% $SiO_2$, 22.8% $TiO_2$, 15.7% $P_2O_5$, 2.0% $CaF_2$, 1.0% $Al_2O_3$, and 0.5% $ZrO_2$, all in percent by weight, at 1,350° C. and casting the melt. The glass material was pressure molded at 750° C. and 20 MPa, but no sufficient deformation occurred. The glass material was heat treated at 840° C. for crystallization to find precipitation of apatite and $MgTiO_3$. The crystallized material had a flexural strength of 120 MPa.

Comparative Example 7

A glass material was prepared by melting a mixture of 35% $SiO_2$, 15% $B_2O_3$, 15% $Al_2O_3$, 20% MgO, 2.5% $K_2O$, 7.5% $Na_2O$, and 5% F, all in percent by weight, at 1,350° C. and casting the melt. The glass material fractured when pressure molded at 750° C.

Examples 22–30

Glass materials containing additives as shown in Table 3 were prepared as in Examples 1–10. The base composition was the same as in Example 1. These glass materials had physical properties as shown in Table 3.

The glass materials were pressure molded. Some glass materials were subject to nucleation treatment by the same procedure as described above prior to pressure molding. Whether or not the nucleation treatment was effected is reported in Table 3 together with the nucleation temperature. A mold and punch for pressure molding were made of a dental investment material Cosmotec Vest (manufactured by GC K.K.). A frustoconical block (height 5 mm, maximum diameter 5 mm, minimum diameter 4 mm) of the glass material was placed in the bore of the mold, which was heated at a rate of 20° C./min. in a split electric furnace SS-1700 (manufactured by Nemus K.K.). After a soaking time of 10 minutes passed, the glass material was pressure molded in the furnace. The molding pressure determined by the method mentioned above was less than 5 MPa for all the glass materials.

Each of glass materials was heat treated in an electric furnace KDFVR7 (manufactured by Ring Furnace) for crystallization, obtaining a test specimen. The heating rate was 5° C./min. while the holding temperature and time are shown in Table 3.

Each sample was examined for precipitated phase, outer appearance, flexural strength, fracture toughness ($K_{IC}$) and semi-transparency. The results are shown in Table 3. The measurement of fracture toughness used a sample of the same dimensions as used in the flexural strength test and having at the center a notch of 0.75 mm deep and 100 μm wide. The semi-transparency was evaluated by placing a sample on printed matter and rated "⊚" when the printed characters were readable with ease and "○" when readable with some difficulty. Good semi-transparency ensures an outer appearance closely resembling natural teeth after staining.

TABLE 3

| | Additive to glass material (wt % based on base composition) | | | | Melting temp. (°C.) | Nucleating temp. (°C.) | Tg (°C.) | Td (°C.) | Tx (°C.) | Molding temp. (°C.) |
|---|---|---|---|---|---|---|---|---|---|---|
| | TiO$_2$ | Ag$_2$O | ZrO$_2$ | CeO$_2$ | | | | | | |
| E 22 | 1 | 0.5 | — | — | 1500 | 700 | 740 | 770 | 880 | 810 |
| E 23 | 5 | 0.5 | — | — | 1500 | none | 753 | 780 | 890 | 810 |
| E 24 | 10 | 0.5 | — | — | 1500 | none | 770 | 800 | 890 | 810 |
| E 25 | 13 | 0.5 | — | — | 1500 | none | 770 | 800 | 890 | 810 |
| E 26 | 15 | 0.5 | — | — | 1500 | none | 785 | 805 | 900 | 810 |
| E 27 | 20 | 0.5 | — | — | 1500 | 750 | 785 | 805 | 900 | 810 |
| E 28 | — | — | 15 | 0.5 | 1500 | 800 | 730 | 790 | 890 | 850 |
| E 29 | — | — | 5 | 0.5 | 1500 | 600 | 720 | 780 | 880 | 850 |
| E 30 | — | 0.5 | 10 | — | 1500 | 770 | 730 | 790 | 870 | 850 |

| | Crystallization | | Flexural strength (MPa) | Precipitated phase | Outer appearance | K$_{IC}$ (MPam$^{½}$) | Semi-transparency |
|---|---|---|---|---|---|---|---|
| | Temp. (°C.) | Time (min.) | | | | | |
| E 22 | 820 | 30 | 275 | diopside | yellow* | 2.5 | ⊚ |
| E 23 | 820 | 30 | 260 | diopside | yellow* | 2.5 | ⊚ |
| E 24 | 820 | 20 | 260 | diopside | yellow* | 2.5 | ⊚ |
| E 25 | 825 | 20 | 250 | diopside | yellow* | 2.4 | ⊚ |
| E 26 | 825 | 20 | 240 | diopside | yellow* | 2.3 | ○ |
| E 27 | 825 | 20 | 240 | diopside | yellow* | 2.3 | ○ |
| E 28 | 820 | 30 | 210 | diopside | yellow* | 2.0 | ○ |
| E 29 | 820 | 40 | 200 | diopside | yellow* | 2.0 | ○ |
| E 30 | 830 | 30 | 220 | diopside | yellow* | 2.2 | ○ |

*natural tooth color

In the examples shown in Table 3, the parts had a crystallinity of 0% by volume at the end of pressure molding and a crystallinity of 30 to 50% by volume at the end of crystallization. In Table 3, Examples 24 to 27 containing 10 to 20% by weight of TiO$_2$ and 0.5% by weight of Ag$_2$O required only a very short time for crystallization.

A glass material sample was prepared from the same glass material as Example 25 shown in Table 3 except that the crystallization conditions were changed as shown in Table 4. These samples were measured for physical properties and examined for semi-transparency and color tone. For comparison purposes, a non-crystallized sample of the same composition was similarly examined. The results are shown in Table 4.

TABLE 4

Physical properties of crystallized glass (Composition of Example 25)

| Crystallizing conditions | omitted | 825° C./10 min. | 850° C./45 min. |
|---|---|---|---|
| Precipitated phase | — | diopside | diopside |
| Density (g/cm$^3$) | 3.03 | 3.10 | 3.13 |
| Shrinkage factor (%) | — | 0.66 | 1.0 |
| Coefficient of thermal expansion (10$^{-6}$/° C.) | 5.9 | 5.9 | 6.4 |
| Flexural strength (MPa) | 120 | 200 | 250 |
| Fracture toughness (PMam$^{½}$) | 0.7 | 1.7 | 2.4 |
| Young's modulus (GPa) | 32.9 | 34.0 | 34.9 |
| Vickers hardness | 640 | 680 | 720 |
| Crystallinity (vol %) | 0 | 20 | 40 |
| Semi-transparency | — | ⊚ | ○ |
| Color tone | — | pale yellow | pale yellow |
| Mean grain size (μm) | — | 0.05 | 0.1 |

Examples 31–36

Glass materials of the composition shown in Table 5 were prepared as in Examples 1–10. The amounts of additives are expressed in percents by weight relative to the total of CaO+SiO$_2$+MgO=100% by weight. The glass transition temperature (Tg), crystallization temperature (Tx) and melting point (mp) of the glass materials are also shown in Table 5. The glass materials were subject to heat treatment (1) and heat treatment (2) as shown in Table 5 in this order for crystallization. The crystallized glass materials had a crystallinity of 30 to 70% by volume and the crystalline phase was of diopside. The glass material samples were of the same dimensions as in Examples 11 to 20. The crystallized glass materials were measured for Vickers hardness, flexural strength, machinability, color tone, luster and semi-transparency. The measuring methods and evaluation criteria are shown below.

Vickers Hardness

A Vickers hardness meter was used.

Flexural Strength

Measurement was done as in Examples 11–20.

Machinability

A sample was perforated with a carborundum drill with a diameter of 1.5 mm. The sample was rated "⊚" when drilling was quite easy, "○" when easy, and "Δ" when drilling was possible.

Color Tone

A sample was rated "⊚" when it had a color identical with natural teeth, and "○" when close to natural teeth.

Luster

A sample was rated "⊚" when it had a luster identical with natural teeth, and "○" when close to natural teeth.

Semi-transparency

Evaluation was the same as in Examples 22–30.

The results are shown in Table 5.

Comparative Example 8

A hydroxyapatite (HAP) sample of the same dimensions as in Examples 31 to 36 was prepared and similar measurement and evaluation were done. The results are also shown in Table 5.

Comparative Example 9

A titanium (Ti) sample of the same dimensions as in Examples 31 to 36 was prepared and similar measurement and evaluation were done. The results are also shown in Table 5.

Using a mold and punch assembly of the combination shown in Table 6, pressure molding was repeated 100 times. Combination No. 8 wherein both the mold and punch were made solely of high compression strength material (Cosmotec Vest II) was free of cracks, but when the molds were destroyed with a tool for withdrawal of the molded

TABLE 5

| | Base composition (total 100 wt %) | | | Additives (wt % based on base composition) | | | Tg (° C.) | Tx (° C.) | mp (° C.) |
|---|---|---|---|---|---|---|---|---|---|
| | CaO | MgO | SiO$_2$ | TiO$_2$ | ZrO$_2$ | others | | | |
| E 31 | 25.9 | 18.5 | 55.6 | 13.0 | 1.4 | Ag$_2$O (0.7) | 770 | 920 | 1400 |
| E 32 | 25.9 | 18.7 | 55.4 | 13.9 | 0 | Ag$_2$O (0.7) | 770 | 890 | 1400 |
| E 33 | 25.9 | 18.5 | 55.6 | 7.4 | 5.8 | AgCl (0.7) | 770 | 950 | 1400 |
| E 34 | 25.9 | 18.5 | 55.6 | 13.9 | 0.6 | Ag$_2$O (0.7) | 770 | 910 | 1400 |
| E 35 | 25.0 | 21.5 | 53.5 | 12.7 | 0.9 | AuCl$_3$ (0.5) | 770 | 930 | 1400 |
| E 36 | 25.9 | 18.5 | 55.6 | 9.4 | 1.0 | Ag$_2$O (0.5) | 770 | 940 | 1400 |
| CE 8 | HAP Sintered body | | | | | | | | |
| CE 9 | Ti | | | | | | | | |

| | Heat treatment (1) | | Heat treatment (2) | | Vickers hardness | Flexural strength (MPa) | Machin- ability | Color | Luster | Light trans- mittance |
|---|---|---|---|---|---|---|---|---|---|---|
| | Temp. (° C.) | Time (min.) | Temp. (° C.) | Time (min.) | | | | | | |
| E 31 | 770 | 20 | 850 | 30 | 550 | 370 | ◎ | ◎ | ◎ | ◎ |
| E 32 | 770 | 20 | 810 | 60 | 600 | 320 | ○ | ◎ | ◎ | ◎ |
| E 33 | 770 | 20 | 890 | 30 | 640 | 220 | ○ | ○ | ○ | ○ |
| E 34 | 770 | 20 | 850 | 30 | 570 | 350 | ◎ | ◎ | ◎ | ◎ |
| E 35 | 770 | 20 | 810 | 60 | 500 | 350 | ◎ | ◎ | ◎ | ◎ |
| E 36 | 770 | 20 | 830 | 60 | 540 | 340 | ◎ | ◎ | ◎ | ◎ |
| CE 8 | — | — | — | — | 370 | 100 | Δ | x | x | ○ |
| CE 9 | — | — | — | — | — | — | Δ | x | x | x |

The crystallized glass material samples of Examples 24, 25, 26, 28, 29, and 30 were also examined for machinability by the same procedure as above. They were all rated excellent.

Molding Assembly with Reinforcement

Using a mold having a high strength liner in the cavity as shown in FIG. 11 and a punch having a reinforcement as shown in FIG. 13(a) or a punch made solely of high strength material, pressure molding was done as in Example 1. The materials for the mold and punch and the high strength materials for the mold liner and punch reinforcement are shown in Table 6. For comparison purposes, pressure molding was similarly done using a mold and punch of the same material (Combination Nos. 8 and 9). The compression strength (CS) of these materials are shown in Table 6.

parts, some parts were ruptured. Occurrence of ruptured parts was 5%. In combination No. 9 wherein both the mold and punch were made solely of low compression strength material (Univest), cracks occurred in the mold where glass could penetrate, resulting in burrs on the molded part. Occurrence of defective parts was 5%.

In combination Nos. 1 to 7 wherein the mold and punch satisfied the general and preferred requirements of the invention, neither rupture of the molded parts nor cracking of the molds was observed.

Using the mold and punch mentioned above, the following compositions were press molded by the same procedure as Example 1.

TABLE 6

| Combi- nation No. | Mold Material | CS (MPa) | Mold liner Material | CS (MPa) | Punch material | Punch reinforce- ment material |
|---|---|---|---|---|---|---|
| 1 | Univest (Silky) | ~12 | iron | * | Uni vest | iron |
| 2 | Snow white | ~8 | stainless steel | * | Snow white | stainless steel |
| 3 | Ceravest G | ~10 | alumina | ~2000 | Ceravest G | alumina |
| 4 | Ceravest G | ~10 | Cosmotec Vest II | ~50 | Cosmotec Vest II | — |
| 5 | Ceravest G | ~10 | P.L.V. (smile) | ~35 | P.L.V. | — |
| 6 | Ceravest G | ~10 | zeolite | ~100 | Ceravest G | zeolite |
| 7 | Cristobalite Q | ~6 | porcelain | ~150 | Cosmotec Vest II, CS | ~50 MPa |
| 8** | Cosmotec Vest II | ~50 | — | | Cosmotec Vest II | — |
| 9** | Uni vest (Silky) | ~12 | — | | Uni vest | — |

*not ruptured under a pressure of 20 MPa
**comparison

TABLE 7

| Vitrification | | | | Press molding | |
|---|---|---|---|---|---|
| SiO₂ | CaO | MgO | Temp. | Glass temp. | Molding |
| 63.0 | 29.0 | 8.0 | 1500° C. | almost crystallized | 1000° C. | OK |
| 61.0 | 27.0 | 12.0 | 1500° C. | almost vitrified | 950° C. | OK |
| 52.0 | 41.0 | 7.0 | 1500° C. | almost crystallized | 980° C. | NO* |

*The glass flowed a little, but did not proceed through the sprue.

The data show that the composition of JP-B 36107/1992 is not prone to press molding.

Similarly, a composition composed of 55.6% of SiO₂, 25.9% of CaO, and 18.5% of MgO and having added thereto 10% of TiO₂ and 0.5% of AgNO₃, based on 100% by weight of the SiO₂/CaO/MgO base, was press molded at different temperatures using the following investment compound.

TABLE 8

| Molding conditions | Observation | Investment compound |
|---|---|---|
| 910° C./20 min. | satisfactorily molded/crystallized | Cosmotec Vest |
| 980° C./10 min. | satisfactorily molded/crystallized | Cosmotec Vest |
| 1050° C./10 min. | molded, but reacted with investment | Cosmotec Vest |

The glass reacted with the investment compound at a temperature of 1050° C., resulting in a rough surface, bubbles and cracks.

The benefits of the invention are evident from the foregoing data.

Japanese Patent Application Nos. 5-139079, 5-214944, 5-353680, and 6-80966 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing a molded glass material comprising:
   (1) obtaining a glass material prepared by quenching a molten mass of glass raw materials,
   (2) pressure molding the glass material at a temperature equal to or above its glass transition temperature but below its melting point, and at a pressure of up to 20 MPa, and
   (3) effecting crystallization treatment on the glass material during or after the pressure molding to produce a crystallinity of at least 10% by volume in said molded glass material, wherein said glass material is selected from those from which at least one of CaO—MgO—2SiO₂ (diopside), CaO—MgO—SiO₂ (monticellite), 2CaO—MgO—2SiO₂ (akermanite), 2(Mg,Ca)O—SiO₂ (forsterite), β-(Ca,Mg)O—SiO₂ (wollastonite), Na₂O—Al₂O₃—2SiO₂ (nephelite), Na₂O—Al₂O₃—6SiO₂ (albite), Na₂O—Al₂O₃—4SiO₂ (jadeite), MgO—TiO₂, Al₂O₃—SiO₂ (andalusite), 3Al₂O₃—2SiO₂ (mullite), CaO—Al₂O₃—2SiO₂ (anorthite), 2CaO—Al₂O₃—SiO₂ (gehelenite), and 3CaO—Al₂O₃—3SiO₂ (grossularite) can precipitate out, and wherein apatite cannot precipitate out.

2. The method of claim 1, wherein said glass material prior to pressure molding has a first crystallinity and said molded glass material has a second crystallinity greater than said first crystallinity.

3. The method of claim 1 wherein said glass material has a crystallization temperature and a softening point which is lower than the crystallization temperature and exhibits viscous flow at temperatures below its melting point.

4. The method of claim 1 which further comprises the step of nucleating the glass material prior to the crystallization treatment.

5. The method of claim 1 which further comprises nucleating the glass material prior to pressure molding.

6. The method of claim 1 wherein the pressure molding is carried out at a temperature which is not higher than 50° C. above the crystallization temperature of said glass material.

7. The method of claim 1 wherein the glass material during said pressure molding has a crystallinity of up to 50% by volume.

8. The method of claim 1 wherein said pressure molding is carried out at a temperature which is up to 0.8 times the melting point of the glass material.

9. The method of claim 1 wherein the glass material during said pressure molding has a viscosity of up to $10^9$ poise.

10. The method of claim 1 wherein at the end of said pressure molding of the glass material, the pressure is released while the glass material is at a temperature not lower than its glass transition temperature.

11. The method of claim 1 wherein the pressure molding is carried out in a molding apparatus including a mold and a punch, said mold including a mold body and a molding cavity and a bore through which the punch is inserted, the punch having a surface opposed to the bore inner surface, the bore being in fluid communication with said molding cavity through a sprue, wherein
   the glass material is placed in the bore and the punch is urged into the bore against the glass material for effecting pressure molding in the molding cavity.

12. The method of claim 11 wherein the step of effecting crystallization treatment on said glass material is carried out in the molding cavity.

13. The method of claim 11 wherein said mold further includes a vent in fluid communication with said molding cavity.

14. The method of claim 11 wherein said bore is defined by said inner surface which extends substantially parallel to the direction in which pressure during the pressure molding is applied.

15. The method of claim 14 wherein said bore inner surface has a gradient of up to ⅕ relative to the pressure applying direction.

16. The method of claim 14 wherein said mold further includes a liner covering at least a portion of the bore inner surface, said liner being made of a high strength material having a higher compression strength than the mold body.

17. The method of claim 16 wherein a cover forms at least a portion of the surface of said punch opposed to the bore inner surface, said cover being made of a high strength material having a higher compression strength than the mold body.

18. The method of claim 17 wherein said mold body has a compression strength of up to 20 MPa at the end of said pressure molding.

19. The method of claim 17 wherein both said high strength materials have a compression strength of at least 15 MPa.

20. The method of claim 16 wherein said mold body has a compression strength of up to 20 MPa at the end of said pressure molding.

21. The method of claim 16 wherein said high strength material has a compression strength of at least 15 MPa.

22. The method of claim 11 wherein said sprue is inclined relative to the pressure applying direction.

23. The method of claim 11 wherein said sprue has a cross-sectional shape corresponding to the cross-sectional shape of said molding cavity.

24. The method of claim 1 which further includes the step of machining the glass material after the crystallization treatment.

25. The method of claim 1, wherein the glass material is a non-calcium phosphate system composition comprising silicon oxide, calcium oxide, and magnesium oxide.

26. The method of claim 1, wherein the glass material comprises 40–70 weight percent of $SiO_2$, 20–50 weight percent of CaO, and 8–30 weight percent of MgO.

27. The method of claim 1, wherein said pressure molding is carried out at a pressure of up to 5 MPa.

28. The method of claim 1, wherein said pressure molding is carried out at a pressure of up to 1 MPa.

29. The method of claim 1, wherein said pressure molding is carried out at a pressure of up to 0.1 MPa.

* * * * *